United States Patent [19]

Green et al.

[11] 4,141,347
[45] Feb. 27, 1979

[54] REAL-TIME ULTRASONIC B-SCAN IMAGING AND DOPPLER PROFILE DISPLAY SYSTEM AND METHOD

[75] Inventors: Philip S. Green, Atherton; Louis F. Schaefer; Jon C. Taenzer, both of Palo Alto; John F. Holzemer, Mountain View; S. David Ramsey, Jr., Palo Alto; Joe R. Suarez, Fremont, all of Calif.

[73] Assignee: SRI International, Menlo Park, Calif.

[21] Appl. No.: 725,178

[22] Filed: Sep. 21, 1976

[51] Int. Cl.$^2$ .............................................. A61B 5/02
[52] U.S. Cl. .............................. 128/2 V; 128/2.05 F; 128/2.05 Z; 73/627; 358/112
[58] Field of Search ............... 128/2 V, 24 A, 2.05 F, 128/2.05 Z; 73/67.8 S, 627; 358/112; 340/1 R

[56] References Cited

U.S. PATENT DOCUMENTS

| | | | |
|---|---|---|---|
| 3,555,888 | 1/1971 | Brown | 128/2 V |
| 3,777,740 | 12/1973 | Hokanson | 128/2 V |
| 3,856,985 | 12/1974 | Yokoi et al. | 128/2 V |
| 3,888,238 | 6/1975 | Meindl et al. | 128/2 V |
| 3,896,788 | 7/1975 | Sato | 128/2.05 F |
| 3,922,911 | 12/1975 | Groves et al. | 128/2.05 F |
| 3,987,673 | 10/1976 | Hansen | 128/2.05 F |
| 4,010,634 | 3/1977 | Baumgartner | 128/2 V |
| 4,033,335 | 7/1977 | Nickles | 128/2 A X |
| 4,045,815 | 8/1977 | Griffith et al. | 340/324 AD |

OTHER PUBLICATIONS

Evans, T. C. et al., "Development of High-Resolution UTS Imaging Techniques for Detection and Clinical Assessment of Cardiovascular Disease", prepared by the Mayo Foundation for Natnl. Hrt. & Lung Inst. as report No.-HT-4-2904-1, pp. 8, 34, 9/5/74.
"Pulsed Ultrasonic Doppler Blood-Flow Sensing", Baker, IEEE Transactions on Sonics and Ultrasonics, vol. Su-17, #3, Jul. 1970, pp. 170-184.
"Radio Shack Dictionary of Electronics", Graf, Howard Sams & Co., Indianapolis, 1972, p. 70.
"TTL Cookbook", Lancaster, Howard Sams & Co., Indianapolis, 1974, pp. 131, 162-163.
"Human Carotid Artery Diameter and Flow by a Non-Invasive Technique", Olson and Cooke, Med. Instr. V9#2, Mar.-Apr. 1975, pp. 99-102.
"A Non-Destructive Ultrasonic Technique to Measure Diameter and Blood Flow in Arteries", Olson and Cooke, IEEE Trans. on Biomed Engr., vol. BME-21, No. 2, pp. 168-171, Mar. 1974.
"Ultrasonic Duplex Echo-Doppler Scanner", Barber, Baker, Nation, Strandness & Reid, IEEE Trans. on Biomed Engr., vol. BME-21, No. 2, Mar. 1974, pp. 109-113.

*Primary Examiner*—Robert W. Michell
*Assistant Examiner*—Francis J. Jaworski
*Attorney, Agent, or Firm*—Victor R. Beckman

[57] ABSTRACT

Pulsed real-time B-scan ultrasonic method and apparatus are disclosed together with pulsed Doppler Ulrasonic method and apparatus. The B-scan apparatus includes a pulse operated transmitter and receiver operating at a first frequency, and the Doppler apparatus includes a pulse operated transmitter and receiver operating at a second frequency sufficiently far removed from the B-scan frequency to avoid interference therebetween. A synchronous pulse operation of the B-scan and Doppler systems is provided. The sysem includes a visual display means to which the receiver outputs are connected through a multiplexer operated to pass the B-scan receiver output to the visual display means whenever such B-scan output is present. The Doppler apparatus includes means for temporarily storing the Doppler receiver output, which stored Doppler signals subsequently are read out through the multiplexer to the visual display means between select lines of B-scan display. A simultaneous display of the B-scan image and a Doppler profile is provided when desired. A control stick unit, under one-hand control of the operator, is used to select the position of the line along which the Doppler profile is obtained and displayed. A cursor generator, under control stick control, is used to generate a cursor signal for display of a cursor along which the Doppler profile is displayed. The B-scan apparatus is operable with a normal or magnified display of a section of the object under investigation. Also, a reticle signal generator is included for the display of tick marks at the visual display means.

33 Claims, 18 Drawing Figures

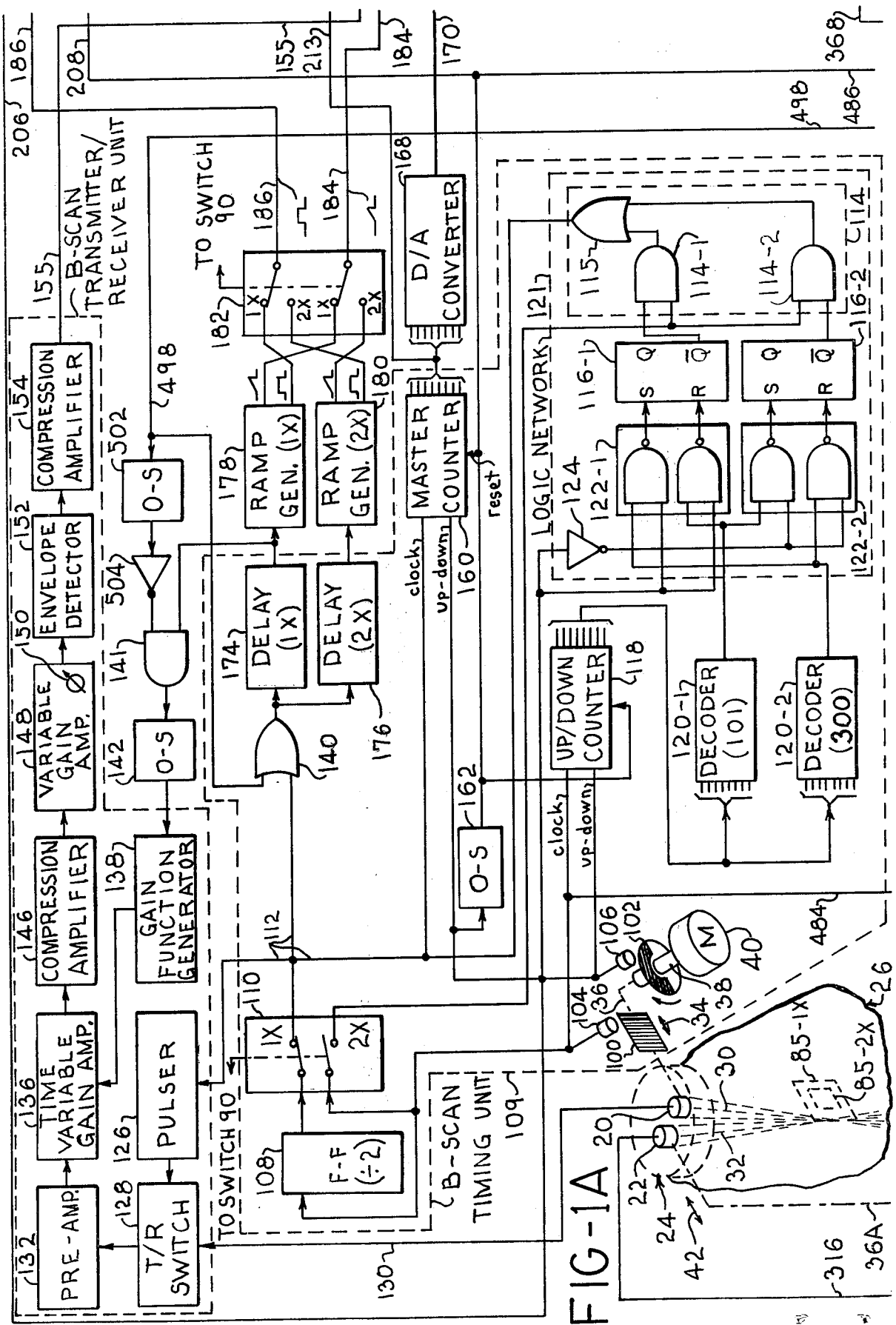

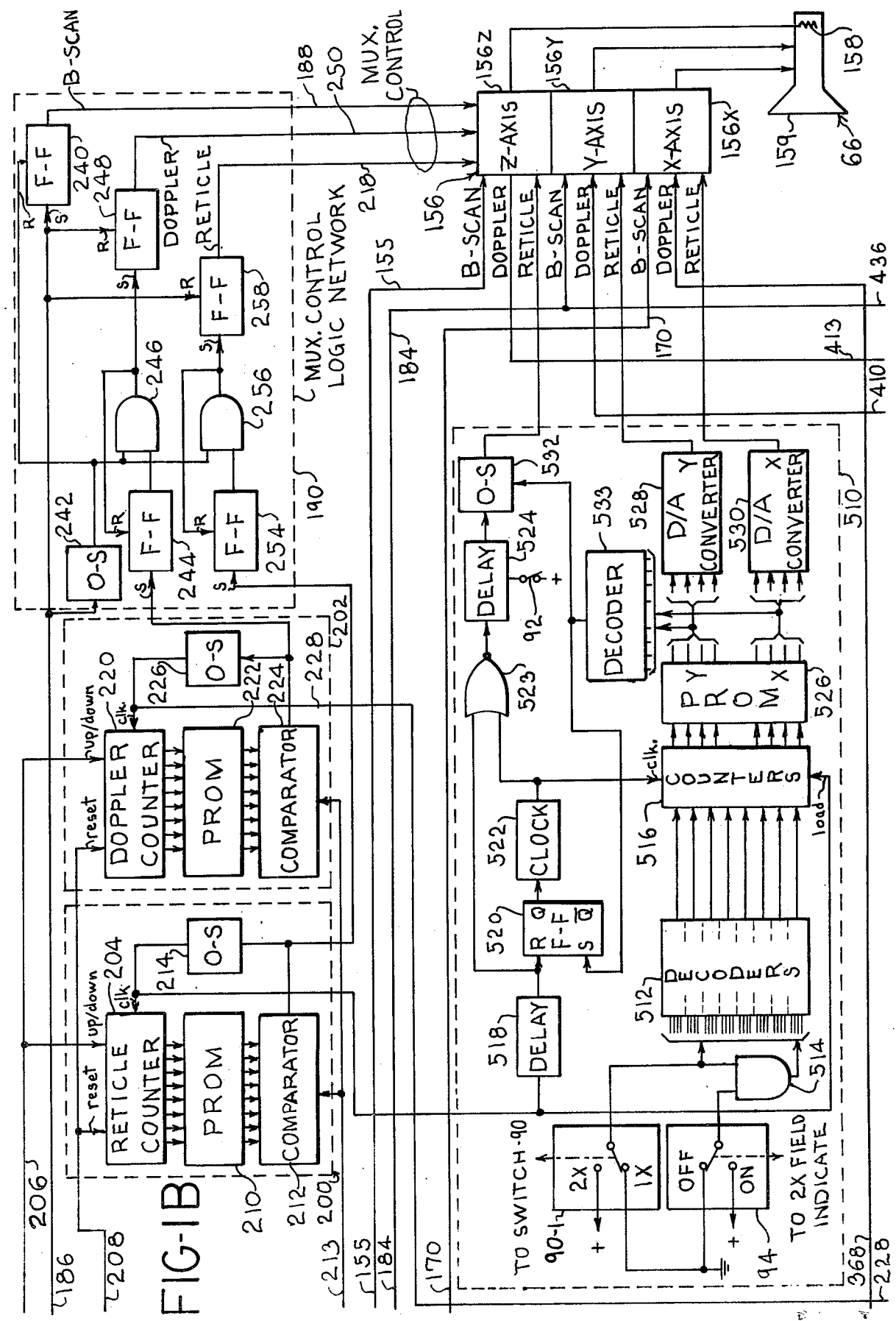

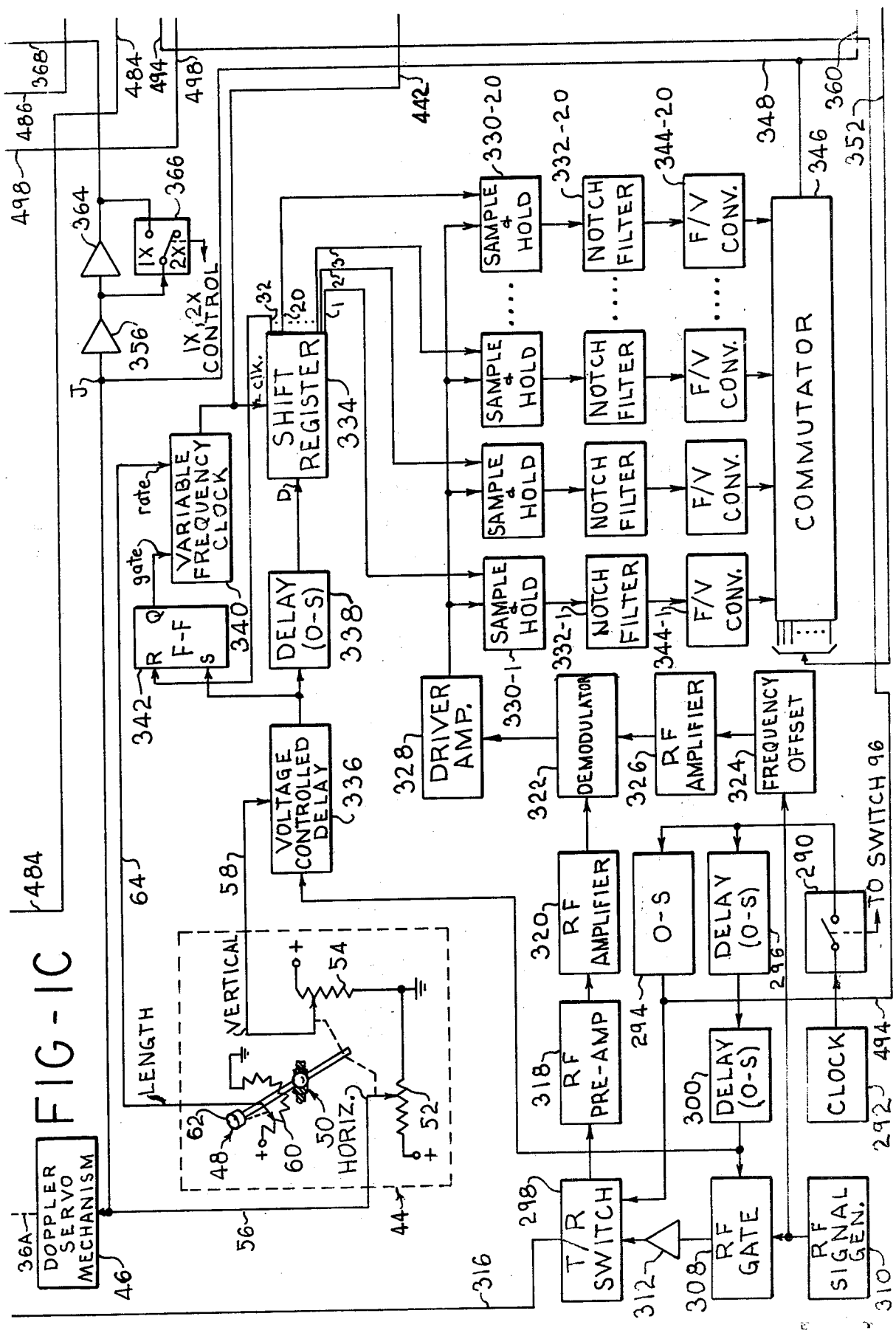

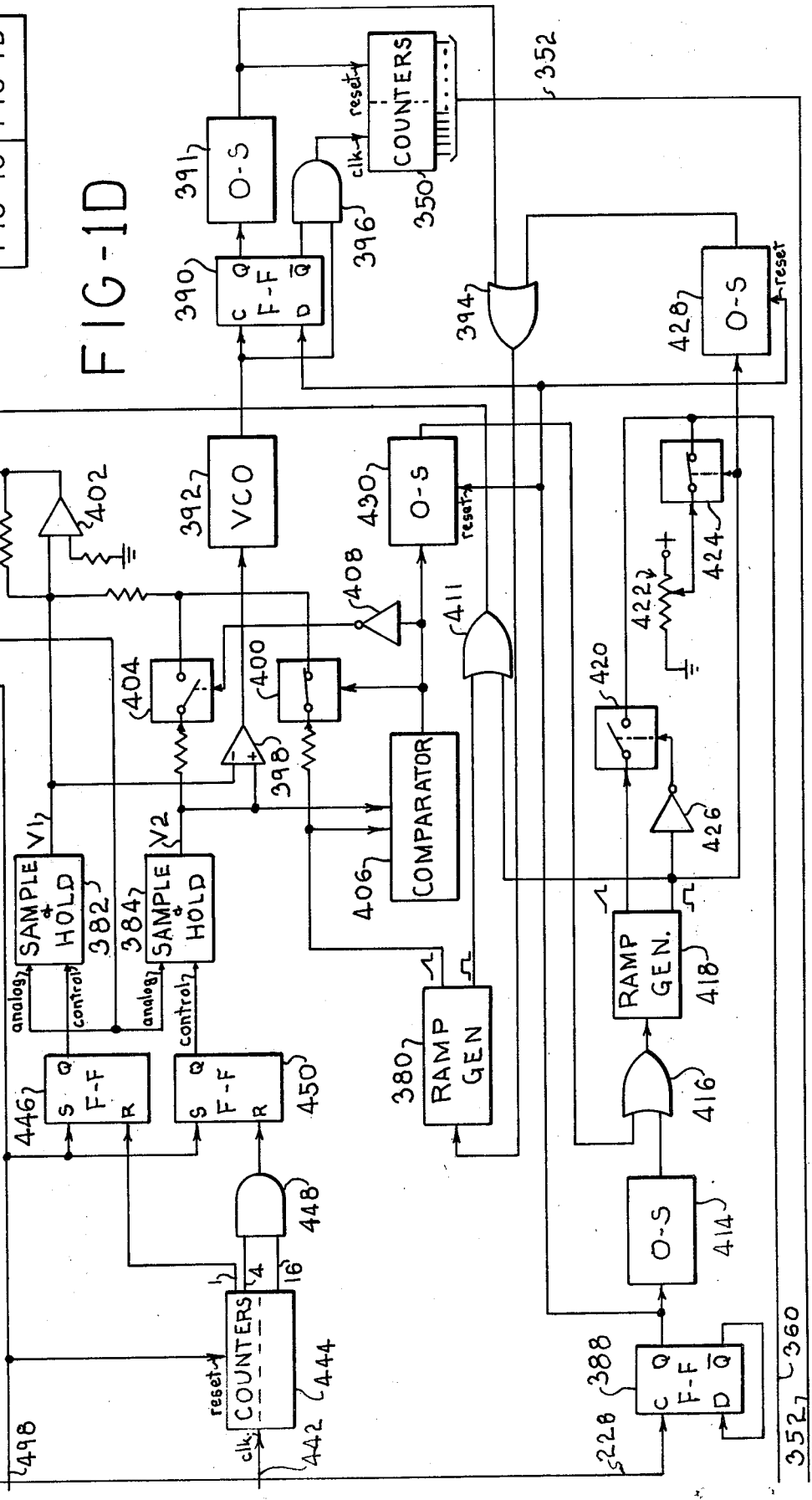

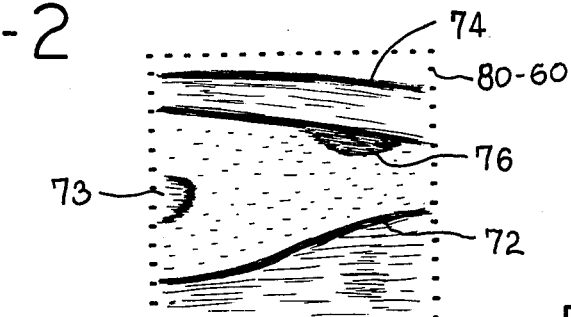
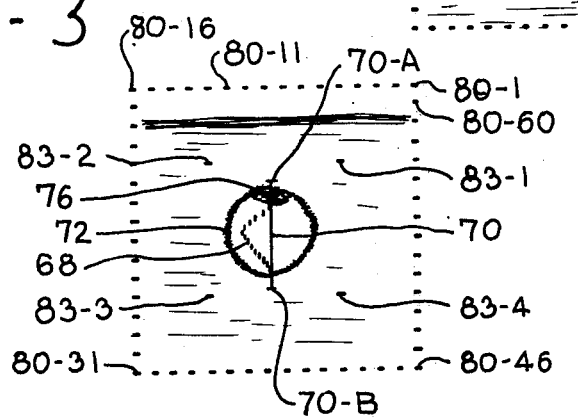
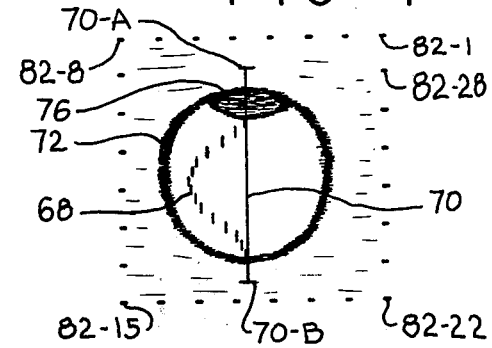
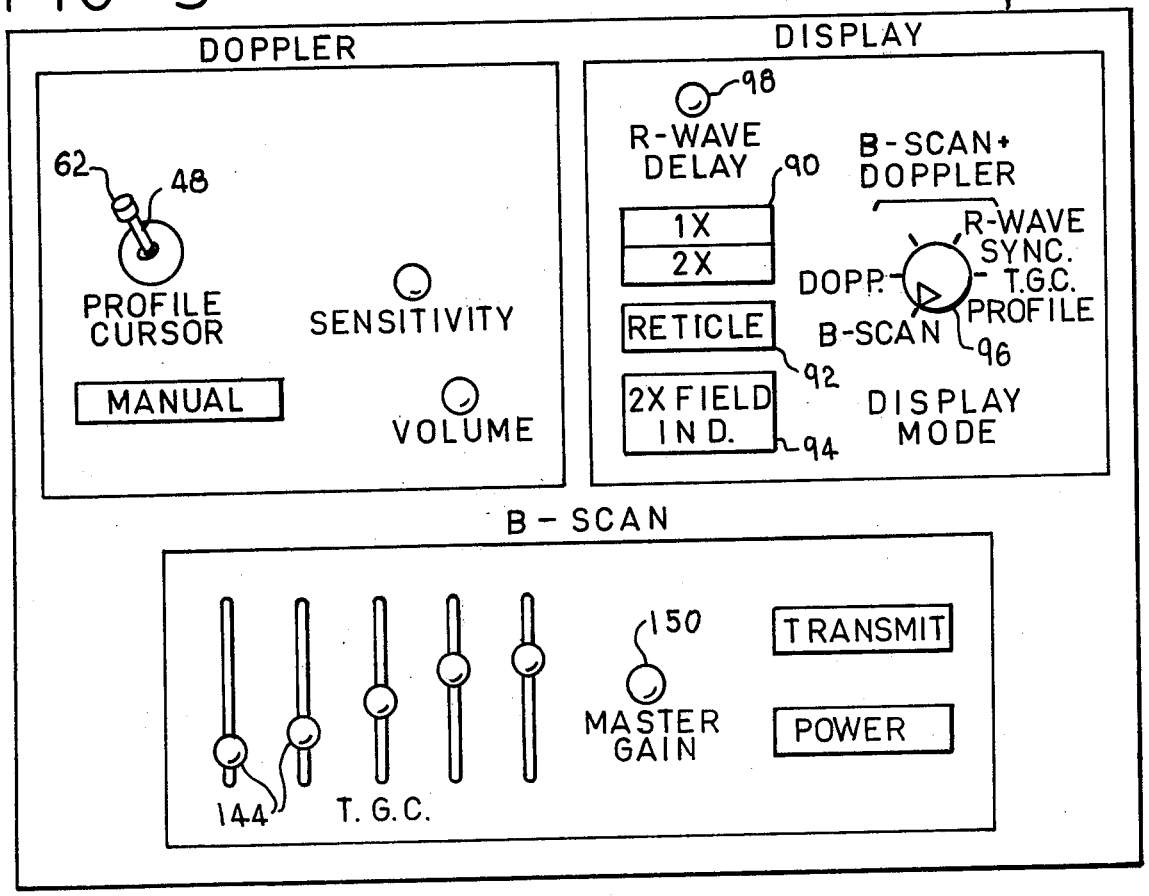

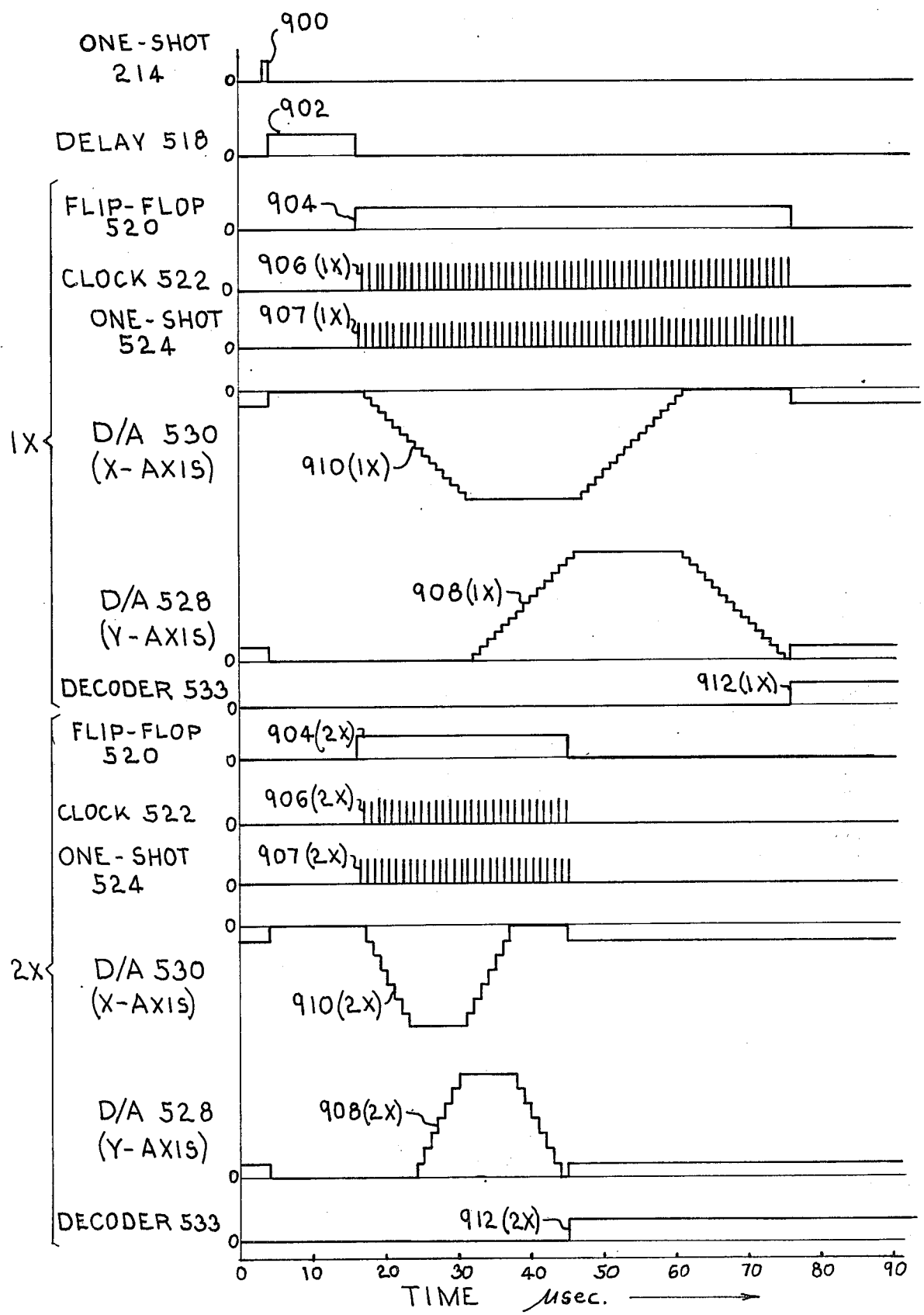

REAL-TIME ULTRASONIC B-SCAN IMAGING AND DOPPLER PROFILE DISPLAY SYSTEM AND METHOD

ORIGIN OF INVENTION

The invention described herein was made in the course of a contract with the Department of Health, Education and Welfare.

BACKGROUND OF INVENTION

This invention relates to ultrasonic imaging method and apparatus and in particular to pulsed real-time B-scan, pulsed Doppler, and a combination pulsed B-scan and pulsed Doppler imaging and motion detecting means for use in the simultaneous display of a B-scan image and blood-flow profile.

The capacity of ultrasonics to differentiate tissues on the basis of their ability to propagate ultrasound, the lack of toxic effects at energy levels required for diagnostic use, and the fact that there is no requirement for invasive techniques with their attendant disadvantages and dangers make ultrasonic visualization a particularly effective and an attractive diagnostic tool. A variety of ultrasonic techniques have been demonstrated, including Doppler and B-scan methods.

The well known pulsed B-scan method employs a narrow beam transducer to project a short ultrasonic pulse into the tissue and to detect the reflected pulses. With B-scan, a two dimensional image is produced by moving the transducer past the area of interest and recording and/or displaying the reflected pulse train at closely spaced intervals. The well known pulsed Doppler method also employs a narrow beam transducer to project a short ultrasonic pulse into moving tissue or particles, such as blood cells, and to detect the frequency of the reflected signal, which frequency is related to the movement or flow of the tissue or particles. By sequentially sampling the reflected Doppler signal a velocity profile along the line of propagation of the transmitted pulse may be obtained. A combined B-scan and Doppler profile display greatly enhances the detection and visualization of the structure under investigation.

A discussion of various ultrasonic techniques, including the well known B-scan method, is found in the INTERNATIONAL JOURNAL OF NONDESTRUCTIVE TESTING, Vol. 1 (1969), pp 1–27, "Methods of Acoustic Visualization", Philip S. Green, one of the present inventors. Ultrasonic pulsed Doppler velocity detection means also are well known as disclosed, for example, in U.S. Pat. No. 3,777,740 by David E. Hokanson, issued Dec. 11, 1973, and in the article entitled, 'Pulsed Ultrasonic Doppler Blood-flow Sensing' by Donald W. Baker in IEEE TRANSACTIONS ON SONICS AND ULTRASONICS, vol. SU-17, No. 3, July 1970. Additionally, a system for manually switching between B-mode and Doppler displays is contained in an article in IEEE TRANSACTIONS ON BIO-MEDICAL ENGINEERING, vol. BME-21, No. 2, March 1974 entitled 'Ultrasonic Duplex Echo — Doppler Scanner' by Frank E. Barber et al. Similarly a combined B-scan and Doppler display is suggested in a report entitled 'Development of High Resolution Ultrasonic Imaging Techniques for Detection and Clinical Assessment of Cardiovascular Disease' dated 9/5/74 by Titus C. Evans, Philip S. Green and James F. Greenleaf, Report No. NO1-HT-4-2904-1 available from National Technical Information Service, 5285 Port Royal Road, Springfield, Virginia, 22151.

SUMMARY OF THE INVENTION AND OBJECTS

An object of this invention is the provision of improved method and apparatus for the diagnosis of cardiovascular diseases, particularly in the carotid and femoral arteries.

An object of this invention is the provision of an improved pulsed B-scan ultrasonic imaging method and apparatus for display of a real-time B-scan image of physical characteristics of a section of the interior of a body.

An object of this invention is the provision of an improved, easily operated, pulsed Doppler blood flow profiling method and apparatus for display of a blood-flow profile.

An object of this invention is the provision of an improved combination pulsed B-scan and pulsed Doppler system for the simultaneous display of a real-time B-scan image of physical characteristics of a section of the interior of a body and of a superimposed Doppler profile along a line of desired length and location substantially in said imaged section.

An object of this invention is the provision of improved method and means for real-time display of ultrasonic B-scan and Doppler information to provide significant clinical data for visualization of the interior of an artery, localization of atheromatous plaque, quantification of the luminal geometry and dimensions, detection of atherosclerotic plaque, differentiation of non-calcified plaque from calcified plaque and from normal tissue, flow velocity, and the like.

The above and other objects and advantages of this invention are achieved by use of separate focused B-scan and Doppler transducers within a mounting head containing a suitable acoustic transmission medium, such as water, and having a liquid-tight acoustic window therein for coupling to the subject under investigation. Asynchronously operating B-scan and Doppler signal transmitters supply recurrent different-frequency pulses to the transducers for launching pulses of ultrasonic waves into the subject. The B-scan transducer is supported for recurrent scanning movement across the section of the interior of the object to be imaged, and the Doppler transducer is supported for movement along a parallel path under control of an output from a control stick unit manually controlled by the operator. Separate B-scan and Doppler signal receivers are provided for processing the received B-scan and Doppler pulse signals reflected from discontinuities, particles, and the like, within the subject. The B-scan receiver output is connected to a visual display means through a multiplexer to provide a real-time B-scan image thereat as video signals are developed at the receiver output. The Doppler receiver, on the other hand, effectively stores electrical analog signals proportional to the Doppler frequency of the echo signal received by the Doppler transducer from along the transducer axis. The analog Doppler proportional signals are sequentially read out through the multiplexer to the visual display means between selected lines of the B-scan frame for the simultaneous display of the B-scan image and Doppler profile. A Doppler cursor signal, to identify the line along which the Doppler profile is obtained, is generated and displayed during alternate Doppler display periods. Once each frame of B-scan operation simultaneous initiation of B-scan and Doppler operations is effected, and first and second deflection voltage levels are established and held, between which levels the Doppler profile and cursor are displayed for assuring proper registration of the B-scan and Doppler displays. Also, the B-scan system functions in different operating modes for display of an image of a section of the subject or for the display of an enlarged image of a portion of said section, both of which displays include the same number of scan lines per frame. During display of the normal size image, tick marks may be provided at the visual display means for indicating the extent of the section imaged when switching to the enlarged image operating mode. The tick marks are supplied by a reticle generator which also is operable between selected B-scan display lines for the display of calibrated tick marks at the margins of the visual display means for tissue metrology.

The invention and the above and other objects and advantages thereof will become apparent from the following detailed description when considered with the accompanying drawings.

BRIEF DESCRIPTION OF THE DRAWINGS

In the drawings, wherein like reference characters refer to the same parts in the several views:

FIGS. 1A, 1B, 1C and 1D, taken together as shown in FIG. 1E, show a simplified combination block and schematic diagram embodying a real-time ultrasonic B-scan/Doppler imaging system and method of this invention;

FIG. 2 is a diagrammatic view of the face of the visual display means showing a B-scan image of a longitudinal section of an artery with the system operating in the 1X mode and with a reticle display;

FIG. 3 is a diagrammatic view of the face of the visual display means which is similar to that of FIG. 2 but showing a cross section of an artery, and simultaneously displaying a 2X indicator together with a Doppler cursor and Doppler profile along said cursor;

FIG. 4 is a view which is similar to that of FIG. 3 but showing the artery at two-times (2X) magnification;

FIG. 5 is a view of the front panel of the imaging system showing various control elements;

FIG. 11 are waveform diagrams for use in explanation of the operation of the reticle generator.

Figure 6:
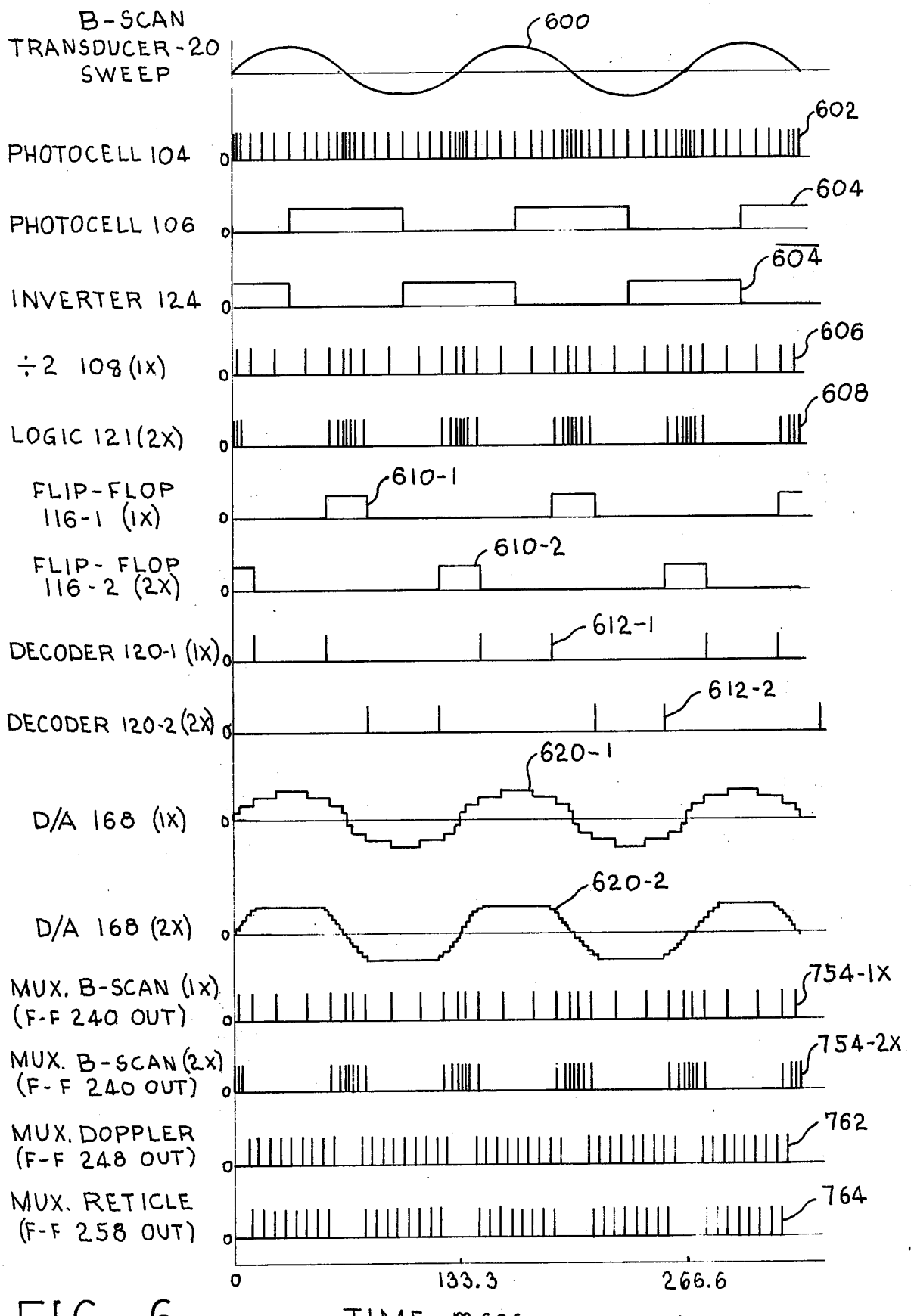
FIGS. 6 and 7 are waveform diagrams of electrical signals developed at various locations within the system for use in explaining the operation of the B-scan portion of the system, the time scale employed in the FIG. 7 waveforms being much shorter than that in FIG. 6.

Reference first is made to FIG. 1A wherein B-scan and Doppler transducer means 20 and 22, respectively, are shown mounted within a scanning head 24 carried at the end of an articulated arm, not shown, for the support thereof over a subject or patient 26. The head contains a suitable acoustic transmission medium, such as water, for the support of acoustic waves produced by the transducer means 20 and 22. A liquid tight acoustically transparent window closes the lower end of the scanning head, through which window ultrasonic compressional waves generated by the transducer means are coupled to the subject 26, and through which reflected acoustical signals returned from the subject are coupled to the transducer means.

For purposes of description, and not by way of limitation, focused transducer means 20 and 22 are employed comprising, for example, lens-focused transducers. The acoustic axes of the transducers 20 and 22 are generally parallel. In the illustrated arrangement, during B-scan operation, the acoustic axis 30 of the B-scan transducer 20 recurrently intersects the acoustic axis 32 of the Doppler transducer 22 within the subject. Also, where the system is employed for the diagnosis and assessment of atherosclerosis of the common carotid artery, for example, lenses which provide focusing at a depth of approximately 1.5 centimeters beneath the skin of the subject 26 and which have a one (1) centimeter depth of focus may be employed. Obviously, the system is not limited to such fixed lens-focused transducers. If desired, the transducers may comprise an array of transducer elements operated so as to provide a variable focus for focusing at different depths for imaging different body parts.

Linear scanning of the B-scan acoustic axis 30 along the subject is provided. In the illustrated arrangement scan operation of the B-scan transducer 20 back and forth across the subject in the direction of the double-headed arrow 34 provides such scanning action. The mechanism for scanning operation of the B-scan transducer is diagrammatically shown comprising mechanical linkage 36 which may include, for example, a crank or eccentric for connection of the transducer 20 to the shaft 38 of a motor 40. Operation of the motor 40 at a constant speed results in a substantially sinusoidal scanning rate of the B-scan transducer 20 across the subject. In the waveforms of FIG. 6, the sinusoidal scanning action of the B-scan transducer is identified by the waveform 600. The ends of the scanning action where the transducer 20 changes direction of movement occur at the peaks and valleys of the waveform 600. The transducer 20 moves at a maximum rate at a point midway between the scan ends at the steepest portion of the sinewave. In practice, the linkage 36 may include, for example, a pantograph-type mechanism driven by the motor 40 for linear traversal by the transducer 20 of the field at a rate of, say, 15 fields (or 7.5 frames) per second. Again, such rates are for purposes of illustration only and not by way of limitation.

The Doppler transducer 22 is movable across the subject 26 in the direction of double-headed arrow 42 along a path parallel with the B-scan transducer 20 and closely spaced therefrom. In accordance with one feature of this invention, positioning of the Doppler transducer 22 along said parallel path is under control of a manually operated control stick type of control unit 44, shown in FIG. 1C. One output from the control unit 44 (the horizontal, or X-axis, position output) is supplied to a servo drive mechanism 46 which, in turn, is connected to the Doppler transducer 22 through a mechanical linkage 36A. The mechanical linkage may be of the same pantographic-type as the linkage 36 used to support the B-scan transducer 20 for movement along a substantially straight line path under control of the servo drive mechanism. As seen in FIG. 1C, the control unit 44 includes a control stick 48 pivotally mounted by a ball and socket mounting means 50 for movement in any pivotal direction. The control stick is mechanically connected to movable arms of Doppler transducer horizontal (X) and vertical (Y) position control potentiometers 52 and 54, respectively, to position the same in accordance with the X and Y positions of the control stick. The potentiometers are supplied with a suitable reference potential, and Doppler horizontal and vertical position potentials are obtained from the movable arms thereof over leads 56 and 58. The lead 56, as noted above, is connected to the servo drive mechanism 46 for horizontal position control of the Doppler transducer 22. The vertical control potential at lead 58 is used to control the vertical position, or depth, within the subject 26 at which Doppler detection along the transducer axis 32 is to begin.

The control unit 44 is provided with a third potentiometer 60 having a movable arm which is mechanically connected to a rotatable knob 62 on the control stick 48 for control of the potentiometer setting by rotation of the knob. The potentiometer 60 provides a Doppler length control potential therefrom over lead 64 for the control of the length of the line at the transducer axis 32 along which Doppler information is acquired for subsequent display of a Doppler profile at the face of a cathode ray tube 66 (FIG. 1B). It will be understood, then, that the information for the Doppler profile display is obtained along a line within the subject 26 determined by the setting of the control unit 44 under one-hand control of the operator. A Doppler profile 68 is shown in the combined B-scan and Doppler displays illustrated in FIGS. 3 and 4. Doppler signal transmitting, receiving and display means are described in detail hereinbelow. For present purposes it will be noted that a cursor 70 is included in the display with the Doppler profile to indicate the line along which the Doppler signal is acquired for such display and to provide a reference for the Doppler profile. The cursor ends are marked by horizontal marks 70A and 70B at the opposite ends thereof.

As noted above, the system may be employed for the diagnosis and assessment of atherosclerosis of the common carotid artery, and generally diagrammatic views of different B-scan and combination B-scan and Doppler displays of the artery of the type which may be provided at the face of the cathode ray tube 66 are shown in FIGS. 2, 3 and 4. FIG. 2 shows a B-scan longitudinal sectional image of the common carotid artery 72, with the artery bifurcation 73 at the left of the display. The skin 74 also is seen in FIG. 2, and clearly appears on the screen since the reflection therefrom is large. As is well understood, the transmitted ultrasonic wavefield is reflected by irregularities and discontinuities encountered thereby, and the discontinuity provided by the skin is great. Blood, however, is more homogeneous than the surrounding tissue and substantially no reflected B-scan signals are obtained therefrom. Consequently, the arterial lumen appears as a light area in the drawings. In practice, the light and dark areas of the drawing would be reversed unless the intensity control signal is inverted to provide for the illustrated type of display. That is, the arterial lumen would appear as a dark area on the screen since substantially no reflected B-scan signals are obtained therefrom. Soft atherosclerotic lesions also may produce relatively low backscattering, making their detection and identification difficult. In FIGS. 2, 3 and 4, plaque 76 is shown faintly at the arterial wall. With the addition of the pulsed Doppler display 68, for the illustrated simultaneous B-scan and Doppler display as shown in FIGS. 3 and 4, the moving blood is readily distinguished from the nearly stationary arterial walls and from lesions protruding into the lumen. The luminal area and shape can be assessed by displaying blood-flow-velocity profiles in relation to their location within the artery.

With the present arrangement, either normal (1X) or two times normal (2X) B-scan image and associated Doppler display may be provided at the face of the cathode ray tube 66, and the labels 1X and 2X are employed hereinbelow to identify components, circuitry, waveforms, illustrative material, and the like, associated with the production and display of the normal and enlarged images, respectively. FIG. 3 illustrates a 1X B-scan display, with Doppler profile, of a cross-section of the artery 72, and FIG. 4 illustrates a 2X display obtained along the same cross-section. Generally, in practice, the system is operated in the 1X mode for locating the area to be investigated, and then is switched to the 2X mode for more detailed investigation.

The system includes a reticle generator used to provide calibrated tick marks along the display margins. For 1X operation (FIGS. 2 and 3) the tick marks are identified by the reference characters 80-1 through 80-60, and for 2X operation (FIG. 4) they are identified by the reference characters 82-1 through 82-28. For purposes of illustration, a 3.0 centimeter by 3.0 centimeter section may be imaged under 1X operating conditions for the visual display of the carotid arteries in the neck. For convenience in operation, the spacing between adjacent tick marks identifies the same distance for both the 1X and 2X operating conditions which, in the illustrated arrangement comprises 0.2 centimeters. For such operation, substantially one-half as many tick marks are required for the 2X display as for the 1X display.

As will become apparent hereinbelow, the section imaged under 2X operating conditions is centrally located with respect to that section imaged under 1X operating conditions. During 1X operating conditions, a 2X field indicator may be provided at the display to indicate the extent of the 2X field when switching from the 1X to the 2X operating mode. Such marks assist the operator in locating the area to be displayed before switching from the 1X to the 2X operating mode. In FIG. 1A, the sections imaged by B-scan operation under 1X and 2X operating conditions are identified by the reference characters 85-1X and 85-2X, respectively.

System operating controls are included at the front panel 86 of the novel apparatus of this invention shown in FIG. 5, where, separate B-scan, Doppler, and Display control sections are shown. The Display control section includes a pushbutton switch 90 for selection of either the 1X or 2X display at the cathode ray tube. A pushbutton operated reticle display switch 92 also is provided for display of the tick marks 80-1 through 80-60 and 82-1 through 82-28 for the 1X and 2X operating modes, respectively. The 2X field indicator tick marks 83-1 through 83-4 are displayed under control of the 2X field indicator switch 94. The Display control section also includes a multiposition display mode selector switch 96 for the display of B-scan only, Doppler only, combined B-scan and Doppler, or for the display of the time gain control profile of time gain control means included in the B-scan system. At another setting of the mode selector switch 96, labeled 'R-wave sync', a synchronization signal derived from a cardiac R-wave detector is supplied to a camera control system for obtaining photographs of the visual display at selected points in the subject's cardiac cycle. The operator may choose the appropriate point in the cardiac cycle by potentiometer control means 98 at the Display control panel for adjusting a delay triggered from the R-wave detector. The control stick 48 with length control potentiometer 62 is shown at the Doppler control section of the front panel. Other front panel controls are described hereinbelow with the description of the associated operating systems. Many of the panel switches include a plurality of switch sections for different functions at various points within the system, and such sections sometimes are individually identified by the use of suitable suffixes in conjunction with the above-identified reference numerals.

As described above with reference to FIG. 1A, the B-scan transducer 20 is swept back and forth in the direction of the arrow 34 with a sinusoidal motion. The pulsed B-scan transmitting and receiving apparatus is operated at a generally sinusoidally varying pulse rate in synchronism with the sinusoidal scan rate of the transducer 20 thereby providing for a raster of evenly spaced scan lines across the face of the cathode ray tube 66 to avoid variations in the intensity of the display which would otherwise result. Master timing pulses for use in control of the B-scan imaging and display operation are provided by timing means associated with the B-scan transducer drive mechanism. In the exemplary arrangement shown in FIG. 1A such timing means includes a timing plate 100 attached to the reciprocating B-scan transducer 20, and a timing disk 102 attached to the motor shaft 38 for synchronous operation of the plate and disk with the transducer. The plate 100 is formed with a plurality of parallel, evenly spaced stripes, or lines, and a photocell 104 adjacent thereto produces signals in response to the lines as the plate reciprocates. For purposes of description only, the plate may be provided with 400 evenly spaced lines for the production of 400 output pulses from the photocell 104 during travel of the transducer 20 from one end of the scan to the opposite end thereof. The pulses are produced, of course, at a sinusoidally varying rate in synchronism with the sinusoidal scan rate of the transducer 20. In FIG. 6, the master timing pulse output from the photocell 104 is identified by the reference numeral 602. For clarity, only about 1/20th of the total number of pulses produced are shown.

During travel of the transducer 20 from one end of the line of scan to the opposite end thereof, one field (one-half frame) of B-scan information is produced and displayed. However, only one-half of the timing pulses produced are used for timing the operation of the B-scan transmitting and receiving operations in both the 1X and 2X operating modes. Consequently, as will become apparent hereinbelow, the B-scan display comprises 200 evenly spaced scan lines per field, or 400 per frame. The scanning sequence is vertically from top to bottom, and horizontally from left to right to left for a complete picture frame of 400 lines, during which the B-scan transducer is mechanically driven back and forth through a complete scanning cycle.

As noted above, timing means includes also the disk 102 attached to the motor shaft 38. In the illustrated arrangement one-half of an annular track on the disk is of one color and the other one-half is of another color. A photocell 106 located adjacent the track produces an output signal in response to one of the colors for the generation of a series of pulses of equal "on" and "off" time periods. For each complete scan cycle of the B-scan transducer 20 a symmetrical squarewave signal 604 is produced having leading and trailing edges at the ends of travel of the B-scan transducer 20, i.e. at the peaks and valleys of the sinewave 600, as seen in FIG. 6. Generation of such a square-wave signal 604 at the appropriate times simply is achieved by the proper physical positioning of the photocell 106 with respect to the rotating disk 102.

The timing signals 602 and 604 from the photocells 104 and 106, respectively, are used in the production of pulses for the time control of the B-scan transmitting, receiving and display operations in a manner now to be described. First, it will be noted that with the illustrated arrangement the mechanical drive system for the B-scan transducer 20 operates the same in both the 1X and 2X operating modes. That is, the mechanical drive system for scan operation of the B-scan transducer 20 operates to drive the transducer at the same rate along the same path in both the 1X and 2X B-scan operating modes. As noted above, for carotid artery visualization, the B-scan transducer 20 may be periodically driven back and forth along a 3.0 centimeter path at the rate of 7.5 cycles per second. Consequently, the master timing pulse output 602 from the photocell 104 is the same in both the 1X and 2X operating modes. As seen in FIG. 1A, the timing pulse output from the photocell 104 is supplied, inter alia, to a flip-flop 108 included in the B-scan Timing Unit 109 which delivers as output one-half the number of input pulses supplied thereto. Consequently, the 400 pulses produced at the photocell 104 output per pass of the B-scan transducer in either direction are reduced to 200 pulses at the output from the divide-by-two flip-flop 108.

The pulse output from the divide-by-two flip-flop 108 is supplied as one input to a transmission gate 110, which gate has as a second input the photocell 104 output. The gate is set for 1X or 2X operation under control of the output from selector switch 90 (FIG. 5). With the gate 110 in the illustrated 1X position the output pulses from the divided-by-two flip-flop 108 are coupled to line 112 for B-scan timing control. In the 2X position of selector switch 90 the photocell 104 output is connected to the line 112 through the gate 110 and a logic network 121, operated in a manner described below, for supply of the same number of timing pulses to the line 112, but in a different timing sequence. In FIG. 6 the 1X output from the gate 110 at line 112 provided by the divide by two circuit 108 is identified by the reference numeral 606, and the 2X output from the logic network 121, also at line 112, is identified by the reference numeral 608.

For simplicity, the transmission gate 110 is shown symbolically as a double-pole double-throw switch but in practice such gate comprises suitable combinations of AND, OR, NAND, and/or NOR gates. In the 1X position of switch 90 no energizing signal is supplied to the gate 110, and the divide-by-two 108 output is connected directly to line 112 therethrough. In the 2X switch position of switch 90 an energizing signal is supplied to the gate 110 for direct connection of the photocell 104 output to the input of a gate network 114 included in the logic network 121 without division.

Operation of the gate network 114 is under control of the output from flip-flops 116-1 and 116-2 which serve to periodically open and close the gate for passage of selected photocell 104 output pulses 602 therethrough for 2X timing control. The flip-flops 116-1 and 116-2 are operated in such a manner to control the gate network 114 for passage of 200 photocell output pulses produced during B-scan transducer travel along the center of the sweep. At opposite ends of the B-scan sweep the gate network 114 is disabled to prevent passage of photocell 104 output pulses therethrough. In FIG. 6 the flip-flop 116-1 and 116-2 outputs are identified by the reference characters 610-1 and 610-2, respectively, and the output from the gate network 114 is identified by the reference numeral 608. It will be seen that 2X timing pulses 608 are provided at the output from the gate network 114 whenever a control pulse is supplied thereto from either one of the flip-flops 116-1 or 116-2 to AND gates 114-1 or 114-2, respectively, included in the gate network. An OR gate 115 connects the outputs from the AND gates to the line 112.

Operation of the flip-flops 116-1 and 116-2 is under control of the fast and slow timing pulses 602 and 604 from the photocells 104 and 106, respectively, through use of an up-down counter 118 and decoders 120-1 and 120-2. The photocell output pulses 602 and 604 are supplied as input and up-down control signals, respectively, to the counter 118 for up-counting during travel of the B-scan transducer in one direction and down-counting during travel thereof in the opposite direction. The counter output is supplied to the decoders 120-1 and 120-2 and as seen in FIG. 6, an output pulse 612-1 from the decoder 120-1 is provided whenever the count from counter 118 passes 101. Similarly, whenever the count passes 300, an output pulse 612-2 is provided from the decoder 120-2.

The decoder 120-1 and 120-2 outputs are supplied to the flip-flops 116-1 and 116-2 through transmission gates 122-1 and 122-2. The slow clock signal 604 from the photocell 106 and an inverted slow clock signal $\overline{604}$ from the photocell 106 through an inverter 124 are supplied as control signals to the gates 122-1 and 122-2 for alternately enabling the same during scan operation in one and the opposite direction, respectively. During B-scan transducer travel in one direction the decoder 120-1 output, at the count of 101, is passed through the enabled gate 122-1 to the reset terminal of the flip-flop 116-1 to reset the same. At the count of 300, the decoder 120-2 output is passed through the enabled gate 122-1 to the set terminal of the flip-flop 116-1 to set the same. During scan operation in the opposite direction the transmission gate 122-2 is enabled by the signal $\overline{604}$ from the inverter 124 while gate 122-1 is disabled. Now, at the count of 300, the decoder 120-2 output is passed through the enabled gate 122-2 to the reset terminal of the flip-flop 116-2 to reset the same. When the count of 101 is reached, while counting down, the decoder 120-1 output is passed through the gate 122-2 to the set terminal of the flip-flop 116-2 to set the same.

As noted above, the flip-flop 116-1 and 116-2 outputs 610-1 and 610-2 (from the $\overline{Q}$ terminals) are supplied as control signals to the transmission gate 114 to enable the same during the center 200 fast clock pulses during B-scan operation in the 2X operating mode to pass the same during both back and forth scanning. The fast clock pulses from the periodically enabled gate 114, which pulses are generated at a sinusoidally varying rate when the gate is enabled, are supplied to line 112 for periodic recurrent pulse operation of the B-scan system in the 2X operating mode.

Except for the novel 1X and 2X timing operation thereof, the B-scan transmitting and receiving means may be of substantially conventional design. In the illustrated arrangement, as seen in FIG. 1A, the B-scan transmitter is shown comprising a pulser 126 which is supplied with recurrent timing pulses (either pulses 606 for 1X operation or periodic recurrent pulses 608 for 2X operation) over line 112 for on-off control thereof. When the pulser is turned on a high frequency energy pulse is generated which is supplied through transmit-receive switch 128 and over line 130 to the B-scan transducer 20 for pulse generation of ultrasonic waves within the transducer head 24, which waves are focused within the subject 26. The B-scan operating frequency differs sufficiently from the Doppler operating frequency to avoid interference therebetween. For purposes of illustration only, the B-scan unit may operate at a center frequency of, say, 10 MHz whereas the Doppler unit may operate with pulse Doppler signals at a frequency of, say, 5 MHz. By operating at such widely different frequencies asynchronous pulse B-scan and Doppler operation is possible and is employed in the illustrated arrangement.

Continuing the description of the B-scan operation, reflected ultrasonic signals from discontinuities within the subject 26 are received by the transducer 20 and supplied over line 130 and through the transmit-receive switch 128 to a preamplifier 132. The transmit-receive switch 128 functions to isolate the transmitted signal from the input to the preamplifier 132. The preamplifier is of the low-noise, broad-band, high-dynamic range type having a good linear gain characteristic over a wide input signal strength range.

The preamplifier output is supplied to a time variable gain amplifier 136 having a gain characteristic which varies as a function of time. With B-scan operation, wherein return signals received from scatterers furthest within the subject 26 experience the greatest attenuation, it is common practice to compensate for such difference in attenuation by time variable gain amplification of the received signal. In the illustrated arrangement the gain of the variable gain amplifier 136 is varied in accordance with the output from a gain function generator 138. Operation of the generator is started following transmission of an ultrasonic pulse, with start of the generator operation being under control of a timing pulse supplied thereto from line 112 through an OR gate 140, a delay unit 174, a normally enabled AND gate 141, and a one-shot 142. With this arrangement, the same delay time is provided between the presence of a pulse at line 112 and the triggering of the gain function generator 138 for both 1X and 2X operations.

The gain function generator 138 simply may comprise a ramp generator with an output signal which functions to increase the gain of the amplifier 136 in proportion to range in a manner to offset the loss of signal caused by acoustic absorption within the subject. In the present arrangement, an adjustable function generator 138 is used having a plurality of controls 144, accessible at the front panel 86 (see FIG. 5) for control of the shape of the generator output. The setting of each of the five controls 144 (comprising potentiometers, for example) determines the amplifier 136 gain during one-fifth of the echo signal duration thereby permitting the operator to tailor the B-scan display as desired, or required. Adjustable gain function generators for control of variable gain amplifiers are well known and require no detailed description. It here will be noted that the gain function generator output, before triggering, is such as to substantially disable operation of the amplifier 136. Consequently, the generator 138 must be triggered by an output from the one-shot 142 to enable operation of the amplifier 136.

The output from the time variable gain controlled amplifier 136 is applied to a broad band compression amplifier 146 comprising, for example, a DC coupled log amplifier with a compression factor of, say, 40 to 60 dB. The compression amplifier 146 is followed by a variable gain amplifier 148 having a gain control 150 for setting the gain thereof.

The variable gain amplifier 148 output is detected by an envelope detector 152 comprising, for example, a full wave rectifier followed by a low pass filter; the detector output signal being related to the envelope of the broad band high frequency signal output from the amplifier 148. The envelope detector output is supplied to a compression amplifier 154 for matching the detected signal with characteristics of the cathode ray tube 66, to which the signal is fed, for proper display of the entire signal range at the cathode ray tube. The compression amplifier 154 output is connected through lead 155 (from FIG. 1A to FIG. 1B) and applied as an input to the Z-axis section 156Z of a multiplexer 156, the output from which multiplexer section is connected to the control grid 158 of the cathode ray tube 66 to intensity modulate the electron beam thereof. It here will be noted that X-axis and Y-axis multiplexer sections 156X and 156Y, respectively, are included through which beam deflection signals are supplied to the cathode ray tube for deflection of the beam in orthogonal directions across the face 159 of the tube. Such multiplexing means are included for the simultaneous display of B-scan, Doppler and reticle signals in a manner described below.

For B-scan operation, cathode ray tube beam deflection in the X, or horizontal, direction is proportional to the position of the B-scan transducer 20 along the scan path, and deflection in the Y, or vertical, direction is proportional to the time elapsed since the last B-scan pulse was transmitted. As noted above, signals from the photocell 104 are used to control the timing of the B-scan transmitter operation and, therefore, may be used in deriving the B-scan Y-axis deflection signal. Since the photocell 104 output signals are derived from the timing plate 100 included in the mechanical scanning mechanism for the B-scan transducer 20, the signals therefrom also may be employed as synchronizing signals in deriving the B-scan X-axis deflection signal.

The horizontal, or X-axis circuit used to produce a deflection signal for deflection of the electron beam across the face of the cathode ray tube in synchronization with the position of B-scan transducer 20 includes an up-down master counter 160 (FIG. 1A) to which the master timing pulses 606 or 608 (FIG. 6), for 1X or 2X operation, respectively, at line 112 are supplied. Up-down counting control of the counter is provided by an output from photocell 106, which output, as noted above, switches at opposite ends of the transducer 20 sweep. The photocell 106 output also is used to trigger a one-shot 162 having an output connected to the reset terminal of the master counter 160. With this arrangement one output pulse is obtained from the one-shot 162 for each complete back-and-forth scan of the transducer 20 for synchronization of the up/down counting and transducer position once a frame.

The output from the master counter 160 is supplied to a digital to analog (D/A) converter 168 for conversion of the digital counter output to an analog signal for use as the B-scan X-axis (horizontal) deflection signal. For 1X operation, the master counter 160 operates at the sinusoidally varying rate of the pulses 606 (FIG. 6) supplied thereto from the photocell 104 through the divide-by-two circuit 108. Consequently, the D/A converter output comprises a step sinewave 620-1 as shown in FIG. 6. For 2X operation, input pulses 608 are periodically supplied to the counter from the photocell 104 through the gates 110 and 114. Now, the D/A converter output comprises, essentially, a stepped sinewave 620-2 with its positive and negative crests clipped (FIG. 6). The stepped sinewave signal 620-1 or 'clipped' stepped sinewave signal 620-2 output from the D/A converter 168 is connected over line 170 from FIG. 1A to FIG. 1B and supplied as one input to the X-axis multiplexer 156X section. The multiplexer section 156X output, as noted above, is supplied to the horizontal deflection system of the cathode ray tube 66 for horizontal deflection of the electron beam in accordance with the multiplexer output.

Figure 7:
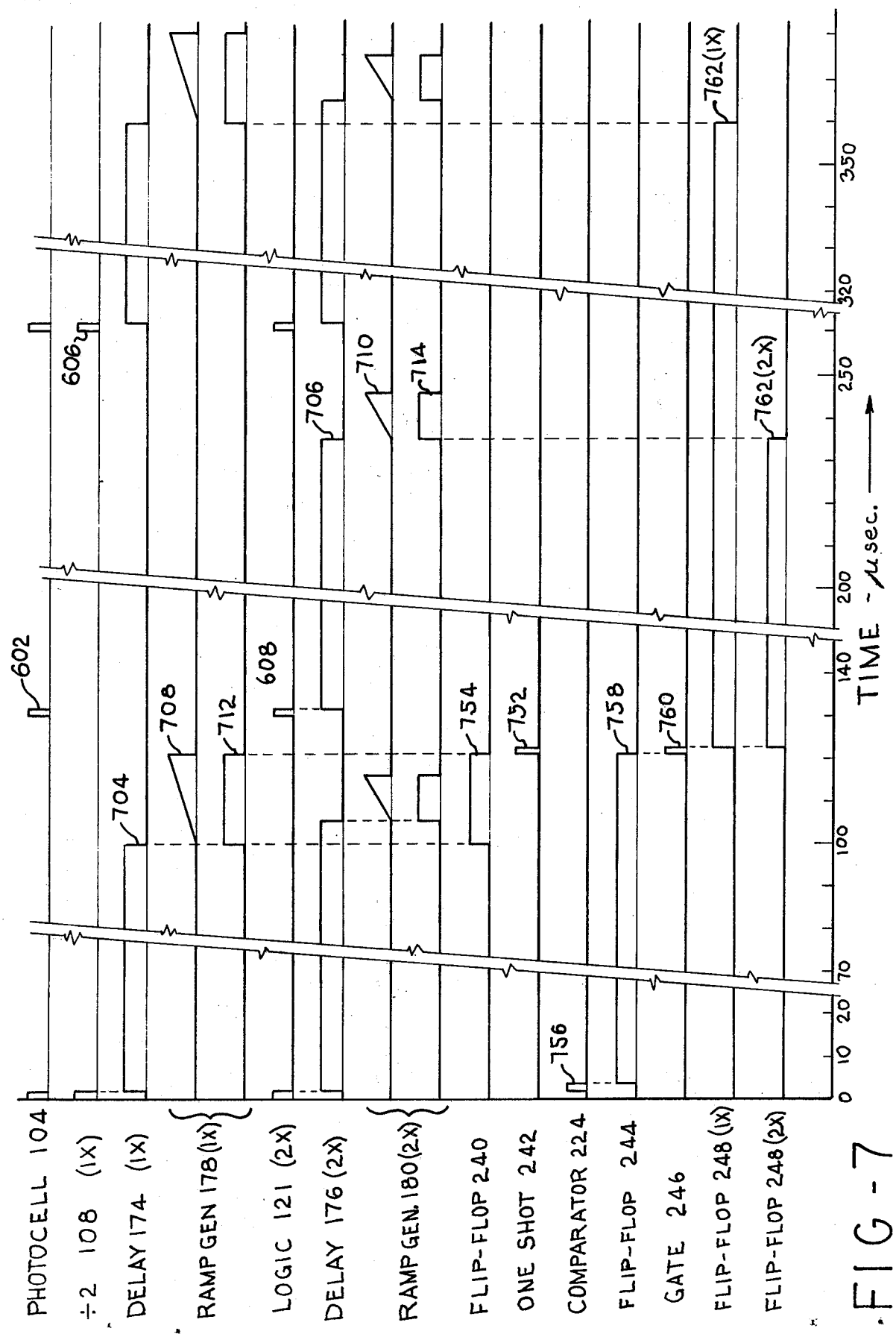

Vertical, or Y-axis, deflection of the cathode ray tube beam for B-scan operation is provided by ramp signals generated following B-scan transmitter operation. A time delay is provided between the transmitter pulse and initiation of the vertical deflection ramp signal, the amount of which delay is dependent upon the transit time of the pulse in traveling from the transducer 20 to the section to be imaged, and the return of the reflected signal to the transducer therefrom. As seen in FIG. 1A, and described above, the imaged section 85-1X for 1X operation begins at a lesser depth and extends to a greater depth than the 85-2X section for 2X operation. Thus, a shorter time delay before initiation of the vertical deflection ramp signal for 1X operation is required than for 2X operation. As seen in FIG. 1A, the master timing pulses on line 112 (either pulses 606 from gate 110 for 1X operation, or pulses 608 from gate 114 for 2X operation) are supplied through the OR gate 140 to the time delay unit 174, for 1X operation, and to a time delay unit 176, for 2X operation. The delay units 174 and 176 simply may comprise one-shots which produce output signals of fixed duration upon receipt of a master timing pulse at the inputs thereto. The outputs from delay units 174 and 176 are shown in FIG. 7 and identified by reference numbers 704 and 706, respectively.

The trailing edge of the pulses 704 and 706 are used to trigger ramp generators 178 and 180, respectively. (In addition, the trailing edge of the 1X delay pulse 704 also triggers the one-shot 142 which triggers operation of the gain function generator 138 which, in turn, controls operation of the amplifier 136 in the B-scan receiver unit, in the manner described above.) The ramp signal outputs from the generators 178 and 180 are identified by reference numerals 708 and 710, respectively, in FIG. 7. The generators 178 and 180 also produce square wave pulses 712 and 714 of a duration equal to the ramp signals 708 and 710, respectively, for use in control of the multiplexer 156 during B-scan operation, in a manner described below. (It will be apparent, with suitable switching and amplifier means for selectively amplifying the output from, say, the ramp generator 178, that only the one ramp generator would be needed for use in the generation of both of the ramp signal outputs 178 and 180 required for the 1X and 2X operations, respectively.) Also, in the illustrated arrangement the delay units 174 and 176 provide for fixed time delays. However, it will be apparent that adjustable delay units may be employed for imaging different depth sections, if desired, to accommodate different sonic pulse times as required.

A transmission gate 182, under control of 1X-2X switch 90 at the front panel 86 (FIG. 5) and illustrated symbolically as a double-pole double-throw switch for simplicity, but comprising a network of gates, is used for selecting either the 1X or 2X ramp and square wave signals for use in the B-scan receiver operation. The selected ramp signal 708 or 710 is supplied over line 184 (from FIG. 1A to FIG. 1B) to the input of the Y-axis multiplexer section 156Y for use as the Y-axis deflection signal during B-scan operation. The selected square wave signal 712 or 714 is supplied over line 186 (from FIG. 1A to FIG. 1B) as one input to a logic network 190 described in detail hereinbelow following a description of the source of Doppler and reticle control signals which also are supplied thereto. For present purposes, it will be understood that the logic network prevents such Doppler and reticle control signals from switching the multiplexer 156 during the presence of the B-scan control signal (712 or 714) on line 186.

The square wave signal 712 or 714 essentially is passed directly through the logic network 190 and supplied over line 188 as a B-scan control signal for the multiplexer 156. B-scan horizontal deflection signal 620-1 or 620-2 (FIG. 6), vertical deflection signal 708 or 710, and the B-scan receiver output from amplifier 154 are simultaneously supplied to the cathode ray tube for the generation of a vertical line of B-scan signal information during the presence of the B-scan channel control signal to the multiplexer over line 188. With the display mode switch 96 (FIG. 5) in the illustrated B-scan position, or in either of the two B + Doppler positions, a B-scan line of information is generated and displayed for each B-scan transmitter pulse produced, (except one during which various operating levels are established to assure that the Doppler display is properly located with respect to the B-scan display). For 1X operation, the vertical B-scan lines are generated at a sinusoidally varying rate, in synchronism with the sinusoidal scanning operation of the transducer 20 for the production of evenly spaced vertical sweep lines at the face of the cathode ray tube 66. With 2X operation, the transmitting and receiving units are periodically operated during the central portion of the transducer 20 scan. During such 2X operating periods, the transmitting and receiving units are operated at a sinusoidally varying rate in synchronism with the central portion of the transducer 20 scanning operation for the production of evenly spaced vertical scan lines. The same number of scan lines are produced during operation over the central portion of the scan of the transducer 20 in the 2X operating mode as are produced during a complete scan thereof in the 1X setting. For 1X operation, wherein, say, 400 ultrasonic pulses at a sinusoidally varying rate are produced during each complete (back and forth) cycle of transducer 20 operation, the time between pulses may vary from a minimum of, say, 220 microseconds to a maximum of one (1) millisecond.

With the present invention, B-scan operation and display in the manner described above without Doppler operation and display, and without reticle display, is provided under operator control by simply setting the Display Mode selector switch 96 to the B-scan position. With the switch 96 set for the B-scan mode, and the switch 90 in the 1X setting, the transducer-containing head 24 may be moved along the patient to any desired section to be imaged. When an area of interest is located, the operation may be switched to the 2X setting to provide the operator with an enlarged image of the central portion of the selected area. If the area of interest is not readily locatable using B-scan alone, the Doppler, or the combined B-scan and Doppler operating mode may be selected. With Doppler operation, movement or flow is readily detected. Blood flow, for example, within an artery may be detected using the Doppler display, or multiplexed B-scan and Doppler display, to aid the operator in the initial location of the artery. The transducer head 24 then may be oriented to provide B-scan imaging of the desired section thereof. In any event, it here will be understood that the novel B-scan method and apparatus above-described has application separate and apart from the Doppler and reticle systems described below.

From the above description, it will be apparent that signals are displayed at the cathode ray tube 66 as they become available from the B-scan receiver. The Doppler transmitting and receiving system, which operates asynchronously with the B-scan system, includes low pass filters which function, essentially, as Doppler profile signal storage means for the storage of the Doppler profile signals, which signals subsequently are read out to the cathode ray tube 66 through the display multiplexer 156 between selected B-scan vertical sweeps. Also, generated reticle signals are displayed, by use of the multiplexer, between other selected B-scan vertical sweeps. Since the B-scan vertical lines are generated and displayed at a sinusoidally varying rate, the Doppler and reticle displays are provided where the B-scan vertical sweep rate is slowest, which is adjacent the opposite ends of the field.

Similar reticle and Doppler display timing units 200 and 202 (FIG. 1B) are employed. The reticle timing unit 200 comprises an up-down counter 204 to which the slow timing control signal 604 (FIG. 6) from the photocell 106 is supplied over line 206 from FIG. 1A to FIG. 1B. Also, a reset signal 866 (FIG. 10A) from the one-shot 162 is supplied to the counter over line 208 from FIG. 1A to FIG. 1B to assure synchronization of the up/down counting and transducer scanning direction. The counter output is used to address a programmable read only memory (PROM) 210 having an output which identifies B-scan lines following which a reticle signal is to be displayed. The output from the PROM is coupled to a comparator 212 having as a second input the output from the master counter 160 connected thereto over line 213 from FIG. 1A to FIG. 1B. The comparator 212 compares the count from the PROM 210 with the count from the master counter 160 and provides an output pulse when the counts are equal.

The comparator output triggers a one-shot 214 having an output which is applied both to the clock input to the counter 204 to step the same and to the reticle generator 510 to trigger operation thereof. It will be seen, then, that the counter 204 is stepped to change the address to the PROM only when the count from the master counter 160 equals the count from the PROM. The PROM is programmed to provide for a pulse output from the comparator 212 at any desired master counter output. For example, outputs may be provided at the counts of 2, 4, 6, 8, 10, 190, 192, 194, 196, and 198, if desired, for subsequent reticle display. The comparator 212 output also is supplied as another input to the logic network 190 which, in turn, controls the operation of the multiplexer 156 in the manner described below. For present purposes it will be understood that with an input signal to the logic network from the comparator 212, an output 764 (FIG. 6) is produced at line 218 therefrom which is supplied as a reticle channel control signal to the multiplexer 156 for a reticle display. The logic network 190 simply delays switching the multiplexer to the reticle channel until the end of an existing B-scan channel control signal. The logic network 190 operation is described below.

The Doppler display timing unit 202 is of substantially identical design as the reticle display timing unit 200 described above. Briefly, the Doppler display timing unit 202 comprises an up-down counter 220 to which the same up/down and reset signals are supplied as are provided to the up-down counter 204. The counter output addresses a PROM 222, the output from which identifies those B-scan lines following which a Doppler signal (either a Doppler cursor or Doppler profile signal) is to be displayed. The PROM output is compared with the master counter 160 output at comparator 224 which supplies an output whenever the counts are equal. Obviously, the PROM 222 is programmed differently than the PROM 210 for the provision of output signals from the comparator at different times. The comparator 224 output is supplied as an input to the logic network 190, and to a one-shot 226. The one-shot 226 output steps the counter 220 and is supplied as a timing signal over line 228 from FIG. 1B to FIG. 1D for use in timing the Doppler profile and cursor displays in a manner described below.

LOGIC NETWORK 190

The logic network 190 for channel control of the multiplexer 156 now will be described. The square wave output 712 or 714 from one of the ramp generators 178 or 180, depending upon the setting of the transmission gate 182, is connected over line 186 (FIG. 1A to FIG. 1B) to the input terminal of a flip-flop 240 included in the logic network 190. The flip-flop 240 is set by the leading edge of squarewave signal 712 or 714 to provide an output 754 (FIGS. 6 and 7) therefrom over line 188 to the multiplexer 156 to control the same for transmission of B-scan input signals therethrough to the cathode ray tube. The trailing edge of the square wave signal 712 or 714 triggers a one-shot 242, the output 752 from which resets the flip-flop 240 to terminate the square wave pulse 754.

Assume now that a signal 756 (FIG. 7) is provided at the output from the Doppler comparator 224 signifying that a Doppler display is to be effected. This signal 756 is supplied as an input to a flip-flop 244 to set the same. The flip-flop 244 output 758 is connected to an AND gate 246, the other input to which is obtained from the one-shot 242. The output from the AND gate therefore remains low until the output 752 from the one-shot is applied thereto. When the gate is enabled, the output therefrom is connected as a reset signal to the flip-flop 244 to reset the same and thereby terminate the pulse 758. The output 760 from the gate 246 also serves to set a flip-flop 248. The flip-flop 248 output 762 (1X) or 762 (2X) is connected over lead 250 as a channel selector signal to the multiplexer 156 to condition the same for passage of Doppler input signals at the input thereof to the cathode ray tube. The flip-flop 248 is reset by the square-wave output 712 or 714 at line 186 when the next B-scan line of information is to be transmitted to the cathode ray tube. It will be seen that the multiplexer is conditioned for passage of Doppler signals (either a Doppler cursor or a Doppler profile) for substantially the entire time period between pulses 712, with 1X operation, or between pulses 714, with 2X operation. In FIG. 6, the reference numeral 762 identifies either the 762 (1X) or 762 (2X) output of the flip-flop 248, depending upon the selected operation.

The reticle comparator 212 output is employed in the same manner as the Doppler comparator 224 output to control the multiplexer 156 for a reticle display. In brief, the comparator 212 output sets a flip-flop 254. The flip-flop 254 output, together with the one-shot 242 output, are supplied as inputs to an AND gate 256, the output from which sets a flip-flop 258. The output from the flip-flop 258 is connected over line 218 to the multiplexer 156 as a channel control signal for passage of reticle input signals therethrough to the cathode ray tube 66. The flip-flop 258 is reset by the next pulse 712 or 714 to occur which, as described above, initiates a B-scan multiplex operation. From the above description, it will be seen that through use of the logic network 190, the multiplexer 156 is controlled for transmission of B-scan signals for the 'real time' display thereof as they become available from the B-scan receiver. Reticle signals produced by the reticle signal generator 510 are displayed between selected lines of the B-scan display as determined by the programming of the PROM 210. Doppler profile signals from the Doppler receiver and Doppler cursor signals from the cursor generator also are displayed between selected lines of B-scan display as determined by the programming of the PROM 222.

DOPPLER TRANSMITTING AND RECEIVING SYSTEM

The pulse Doppler transmitting and receiving system operates asynchronously with respect to the operation of the above-described real-time pulse B-scan system. Asynchronous transmitting operation is made possible by the use of widely different B-scan and Doppler frequency pulse signals so as to avoid interference between the acoustic wave fields. For example, as noted above, the pulsed B-scan system may operate at a relatively high frequency of, say, 10MHz, whereas the pulsed Doppler system may be operated at a much lower frequency of, say, 5MHz. By use of such frequencies, the simultaneous presence of the pulsed signals within the subject, and simultaneous B-scan and Doppler receiver operation is possible without mutual interference.

Figure 8:
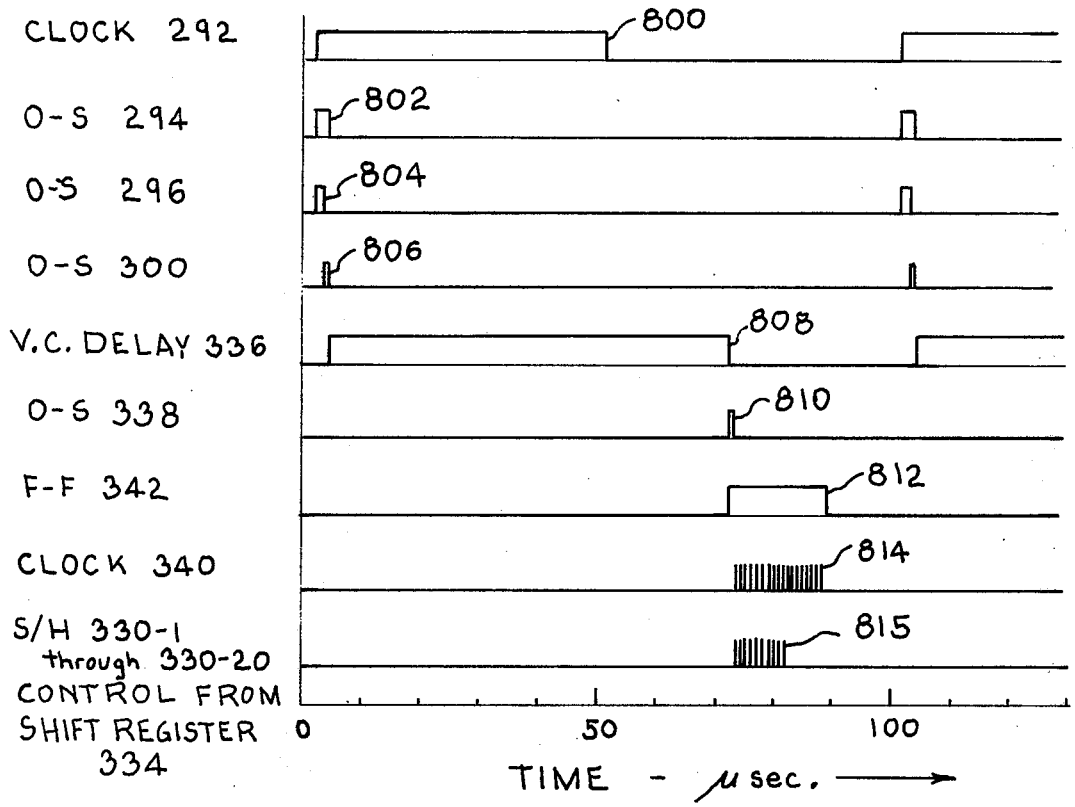
FIGS. 8, 8A, and 8B show waveform diagrams for use in explanation of the Doppler portion of the system during acquisition of Doppler signals.

Except for the timing of the Doppler display means, which is time division multiplexed with the real-time B-scan display, substantially any suitable pulsed Doppler transmitting and receiving system may be employed in the arrangement of this invention. The illustrated Doppler system is of the general type disclosed in the above-mentioned article entitled, "Pulsed Ultrasonic Doppler Blood-Flow Sensing" IEEE Transactions on Sonics and Ultrasonics, SU-17, pp. 170–185 (1970) by D. W. Baker. Referring to FIG. 1C, on-off control of the Doppler system is under control of a transmission gate 290 which, in turn, is controlled by the display mode switch 96 (FIG. 5) for closure thereof when the display mode switch is either in the Doppler or in either of the B + Doppler switch positions. For simplicity, the gate 290 simply is shown as a single pole single throw switch in FIG. 1C. With the gate 290 in the enabled condition, a clock signal 800 (FIG. 8) from Doppler clock 292 is supplied therethrough to first and second one-shots 294 and 296, respectively. The output 802 (FIG. 8) from the first one-shot is used as a control signal to gate on a transmit/receive (T/R) switch 298 in preparation for the transmission of a transmit pulse therethrough. The other one-shot 296 serves as a delay unit for delayed triggering of a one-shot 300. In FIG. 8 the output from one-shots 296 and 300 are shown by waveforms 804 and 806 respectively. The delayed output 806 controls the opening and closing of an RF gate 308 which gate, when enabled, passes the output signal from an RF signal generator 310 to a power amplifier 312. The amplified signal from the power amplifier 312 passes through the now enabled T/R switch 298 and thence through lead 316 to the Doppler transducer 22 in the head 24 (FIG. 1C to FIG. 1A). The RF gate is opened and closed, under clock 292 control, to provide the transducer 22 with phase-coherent 5MHz bursts of, say, 1 microsecond duration at a pulse repetition frequency of, say, 10,000 pulses per second.

The Doppler transducer 22 is located adjacent the path traversed of the B-scan transducer 20, and may be positioned at any point along a parallel path under control of the horizontal output signal at line 56 from the control stick unit 44 in the manner described above. A focused transducer 22 may be employed for focusing of the ultrasonic beam therefrom at a depth substantially equal to the center of the depth range of the B-scan system. Ideally, the beam axis for the Doppler transducer would be in the plane of the section imaged by the B-scan system so that the resultant Doppler display would provide an indication of Doppler response from points within the imaged section 85-1X or 85-2X shown in FIG. 1A. However, since separate B-scan and Doppler transducers 20 and 22, respectively, are employed, alignment of the Doppler axis 32 in the plane of the B-scan imaged section extended is not practical and, is not required. The parallel paths along which the transducers move are closely positioned to minimize the angle at which the Doppler axis 32 intersects the image plane. If desired, the transducers 20 and 22 may be arranged to provide for parallel acoustic axes 30 and 32.

Figure 8A:
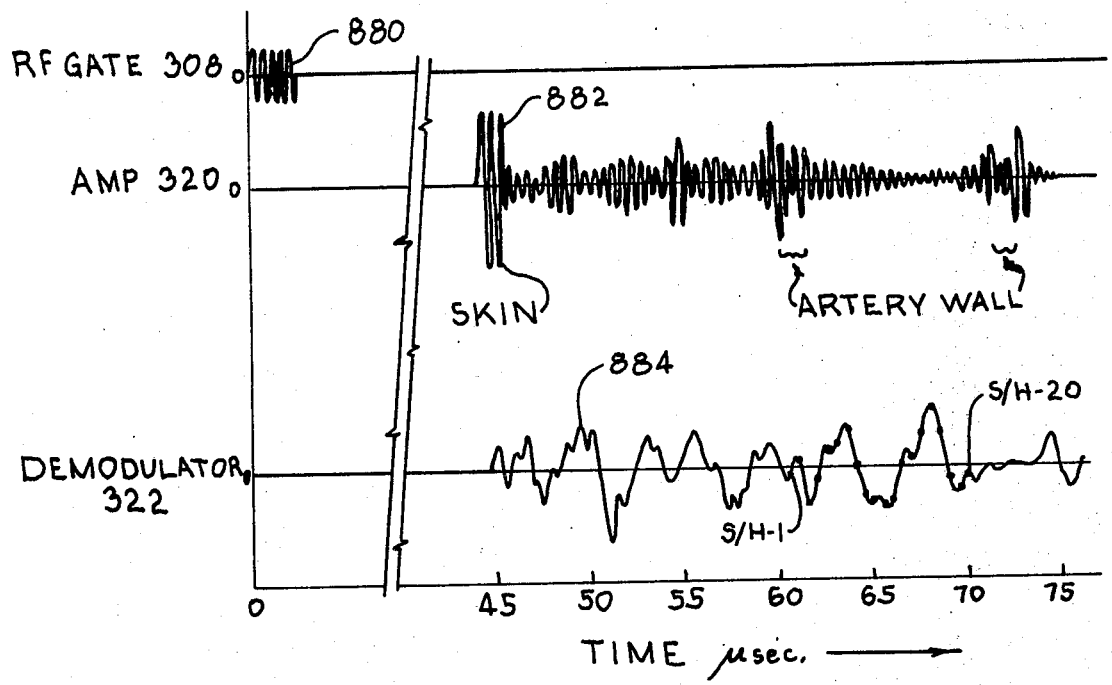

Following transmission of the ultrasonic pulse by the Doppler transducer 22, echo signals from scatterers within the subject 26 are received by the transducer and electrical signal output therefrom is supplied over line 316, and through the transmit-receive switch 298 (now in the 'receive' condition) to a preamplifier 318. The signals from the preamplifier are further amplified by an RF amplifier 320, and the output from the RF amplifier is supplied as one input to a demodulator 322 which has a voltage output related to the Doppler frequency shift of the echo signal. It will be understood that echo signals include those from both stationary and moving scatterers, and that the return signals from moving scatterers, such as blood cells flowing within a vein or artery, are shifted in frequency due to Doppler effects. Depending upon the direction of motion, the signal may undergo an increase or decrease in frequency. Here, a reference signal is supplied to the demodulator from the RF signal generator 310 through a frequency offset circuit 324 and RF amplifier 326. Such a reference signal, which is offset from the transmitted frequency, and phase coherent therewith, is employed to bias the zero flow output voltage position so that reverse flow can be detected and subsequently displayed. The amplitude of the demodulator output signal varies with the relative phase of the echo and reference signals supplied to the demodulator. In FIG. 8A the Doppler transmitter signal 880, the amplified Doppler echo signal 882 from amplifier 320, and the demodulator output signal 884 are shown.

The Doppler signal 884 from the demodulator 322 is amplified by driver amplifier 328 and supplied to a series of sample and hold circuits 330-1 through 330-20 in parallel. Control inputs to the sample and hold circuits are obtained from a shift register 334 for the sequential sampling of the Doppler signal. In the illustrated arrangement a 32-bit serial shift register is employed of which twenty output bits are employed in the control of the twenty sample and hold circuits. Obviously, fewer or additional Doppler channels than the twenty illustrated may be employed. Both the time delay between the transmission of a Doppler pulse signal and the initiation of operation of the shift register 334, and the rate at which the shift register is clocked are under control of the manually operated control unit 44 for setting the Doppler "window". Doppler window control is described below following a description of the operation of the remainder of the Doppler receiver.

Referring again to FIG. 8A, echo signals from the patient's skin and artery wall are identified in the waveform 882 of the amplified echo signal. Also in FIG. 8A, twenty points on the demodulator output 884 are marked to identify the times at which the twenty sample and hold circuits 330-1 through 330-20 are sequentially operated to sample the demodulator output. It will be seen that the Doppler window is positioned for operation within the artery walls for blood flow detection. Note that the demodulator output 884 is only a function of the phase difference between the received rf signal 882 and the offset frequency and not a function of the rf signal amplitude.

Figure 8B:
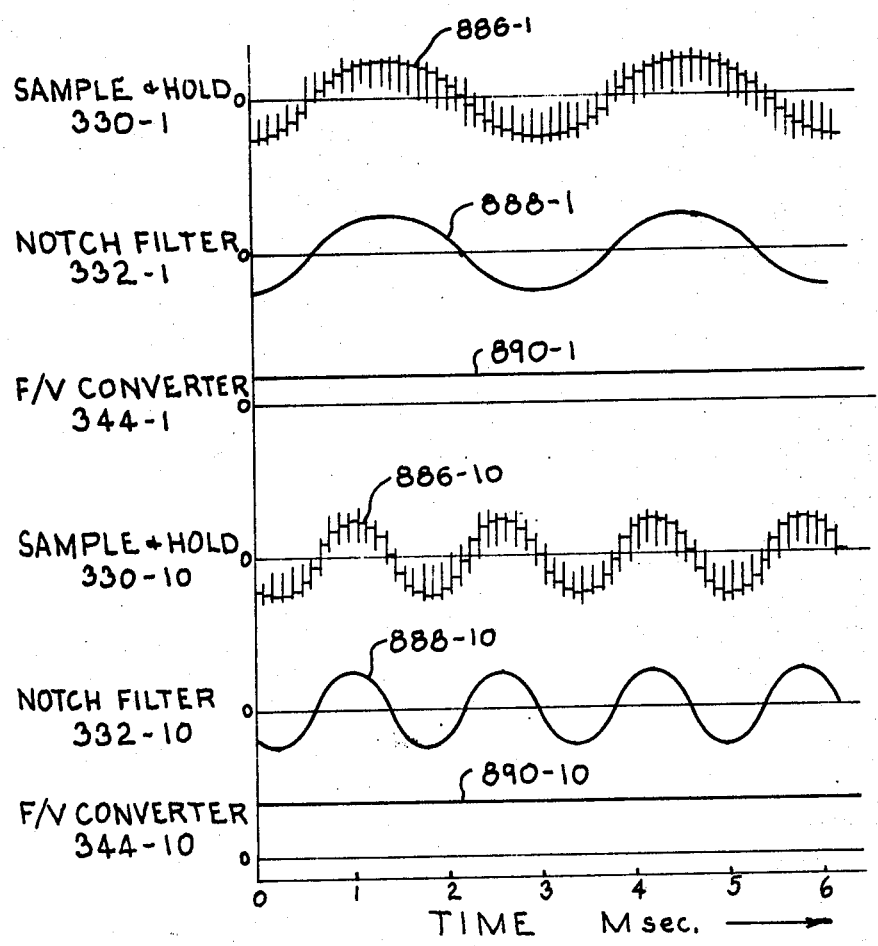

The outputs from the sample and hold circuits 330-1 through 330-20 are fed through notch filters 332-1 through 332-20 to frequency-to-voltage converters (F/V) 344-1 through 344-20. The filter notch for filters 332-1 through 332-20 is set at the difference frequency (fo) between the rf signal frequency and the offset frequency supplied to the demodulator 322 from the frequency offset 324 through the amplifier 326, to prevent most of the difference frequency signal from passing therethrough to the frequency to voltage converters. Filtering at the notch fo is not complete, and a small portion of such signal is allowed to pass through the filter. In the absence of a Doppler frequency echo signal (for example, between the skin and artery) the small difference frequency signal is detected by the frequency to voltage converters for conversion to an analog signal level indicative of zero Doppler return. Also, the filter has low and high cut off frequencies of, say, fo-3KHz and fo+3KHz to eliminate high frequency noise, such as that produced by switching of the sample and hold circuits. In FIG. 8B, outputs 886-1 and 886-10 from two channels of the sample and hold circuits 330-1 and 330-10 are shown, with spikes of noise produced when switching the same. The corresponding filtered outputs 888-1 and 888-10 from the filters 332-1 and 332-10 also are shown in FIG. 8B.

A higher Doppler frequency signal is returned from blood flow near the center of the artery than adjacent the artery wall, and the different Doppler frequency signals are indicated by the different frequency signals from the filters 888-1 and 888-10 in FIG. 8B. The frequency to voltage converters 344-1 through 344-20, which are of the zero-crossing type, convert the signals to corresponding analog signals, two of which 890-1 and 890-10 are shown in FIG. 8B. The analog voltage signals are supplied through a commutator 346 to the cathode ray tube for horizontal deflection during Doppler display.

DOPPLER 'WINDOW' CONTROL

Operating controls for the shift register 334 for setting the Doppler window now will be described.

The RF gate control pulse 806 (FIG. 8), from the one-shot 300 (FIG. 1C) which triggers generation of a Doppler transmitter signal, also is supplied as an input to a voltage controlled delay unit 336 comprising, for example, a one-shot. The output pulse 808 from the voltage controlled delay unit has a duration dependent upon the magnitude of a control voltage supplied thereto over line 58 by the Doppler Y-axis control output from the control stick unit 44, described above. The trailing edge of pulse 808 is used to trigger a one-shot 338, the output 810 from which is supplied to the data input terminal of the shift register 334.

The shift register 334 subsequently is clocked by the output 814 from a gatable, programmable frequency clock 340. The frequency, or clock rate, is set by the Doppler length control output from the control stick unit 44 connected thereto over lead 64. A gate signal 812 for on-off control of the clock 340 is provided by the output from a flip-flop 342. The flip-flop is set by the trailing edge of the pulse 808 from the voltage controlled delay unit 336 for initiating clock operation. The flip-flop 342 is reset by an output from the shift register 334 when the register input pulse supplied thereto from the one-shot 338 is shifted out of the register. As mentioned above, only twenty of the 32 bit outputs from the register 234 (identified by reference character 815) are employed in controlling the operation of the sample and hold circuits 332-1 through 332-20. The clock, however, continues to run until the input bit to the register is shifted out of the register and to the flip-flop 342 to reset the same. It will be seen, then, that the time at which the clock 340 is gated on is determined by the Doppler vertical control voltage on line 58, and the frequency at which the clock operates is determined by the Doppler length control voltage on line 64. As described above, these Doppler vertical and length control voltages serve to position the Doppler receiver "window", during which time the Doppler echo signal is gated by the sample and hold circuits to the frequency to voltage converters. These Doppler control voltages, together with the Doppler X-axis, or horizontal, control voltage at line 56 are selectively set by the operator by use of the control stick unit 44 in the manner described above.

DOPPLER DISPLAY

As seen in FIG. 1C, the frequency to voltage converter outputs are connected to a commutator, or analog multiplexer. Operation of the commutator 346 for the sequential connection of the frequency to voltage converter output signals to the commutator output line 348 is controlled by the output from counters 350 (FIG. 1D), the commutator control signals from the counters to the commutator being supplied over lead wires 352 from FIG. 1D to FIG. 1C. Timing of the operation of the commutator 346 is controlled in a manner described below to assure proper registration of the Doppler profile display 68 with both the cursor 70 display and the B-scan display. For present purposes it will be noted that when the commutator 346 is clocked the Doppler profile signal at the commutator output is connected over line 348 to the summing junction J at the input to an amplifier 356.

The Doppler profile signal from the commutator 346 is supplied as one of three inputs to the amplifier 356. The Doppler horizontal, or X-position, control signal at line 56 from the control stick unit 44 also is supplied thereto and functions as an amplifier offset signal to establish the reference level for the Doppler profile display, and to establish the lateral position of the cursor 70 during cursor display; the cursor and Doppler profile being displayed during alternate Doppler display periods in the manner described below. The cursor 70, as seen in FIGS. 3 and 4, is provided with horizontal end segments 70A and 70B to clearly mark the cursor ends, and the necessary horizontal deflection signals to produce such end segments are supplied as a third input signal to the amplifier 356 over line 360 from the cursor generator shown in FIG. 1D.

The horizontal deflection signals for Doppler display from amplifier 356 are connected to an amplifier 364 having a voltage gain of two (2). The amplifier is included in the circuit in the 2X operating condition, and is bypassed, by transmission gate 366 in shunt therewith, in the 1X operating condition. The output from the amplifier 364, or from amplifier 356 through enabled gate 366, is connected over line 368 (from FIG. 1C to FIG. 1B through FIG. 1A) to the multiplexer 156 as the Doppler X-axis input signal thereto for connection to the horizontal deflection circuit of the cathode ray tube 66 when a Doppler multiplexer channel control signal is supplied thereto over line 250. For present purposes, it will be understood that a Doppler multiplexer channel control signal 762 is present at line 250 for switching to Doppler display whenever a Doppler profile or Doppler cursor signal is provided at the multiplexer input.

Figure 9:
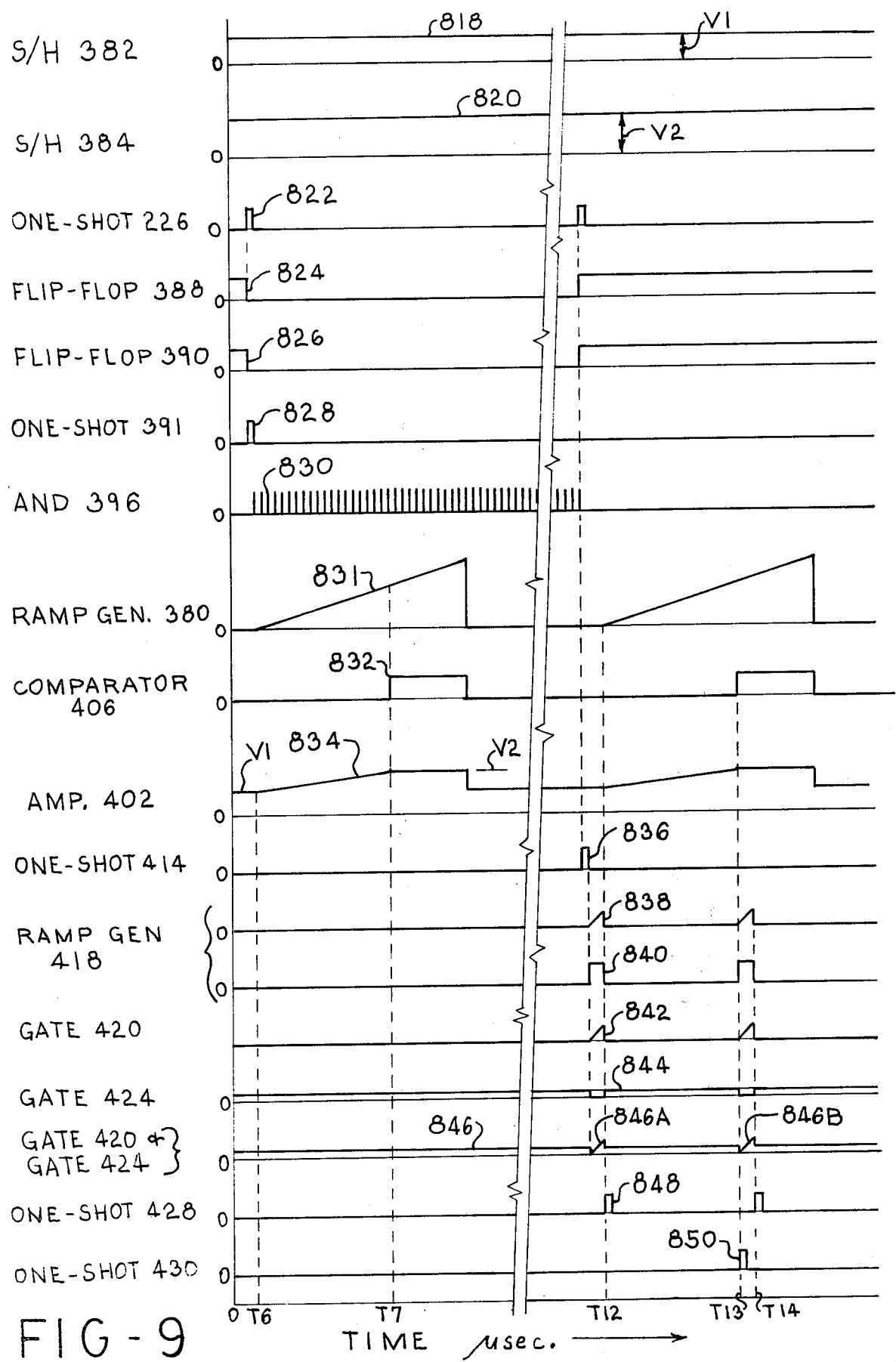
FIG. 9 are waveform diagrams for use in explanation of the operation of the Doppler profile and cursor signal display means.
Figure 10A:
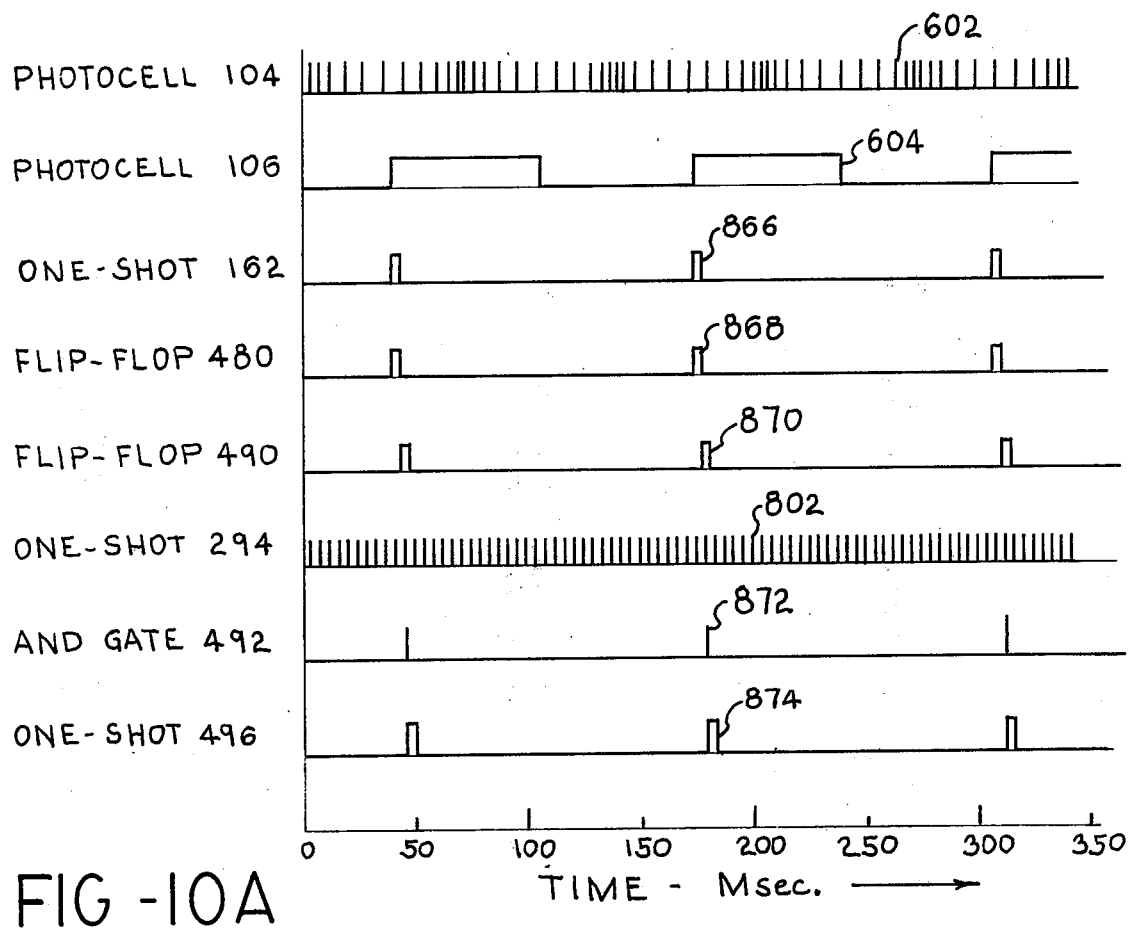
FIGS. 10A and 10B are waveform diagrams for use in explanation of the timing system for assuring proper registration of the Doppler and B-scan displays; the time scale employed in FIG. 10B being much shorter than that in FIG. 10A.
Figure 10B:
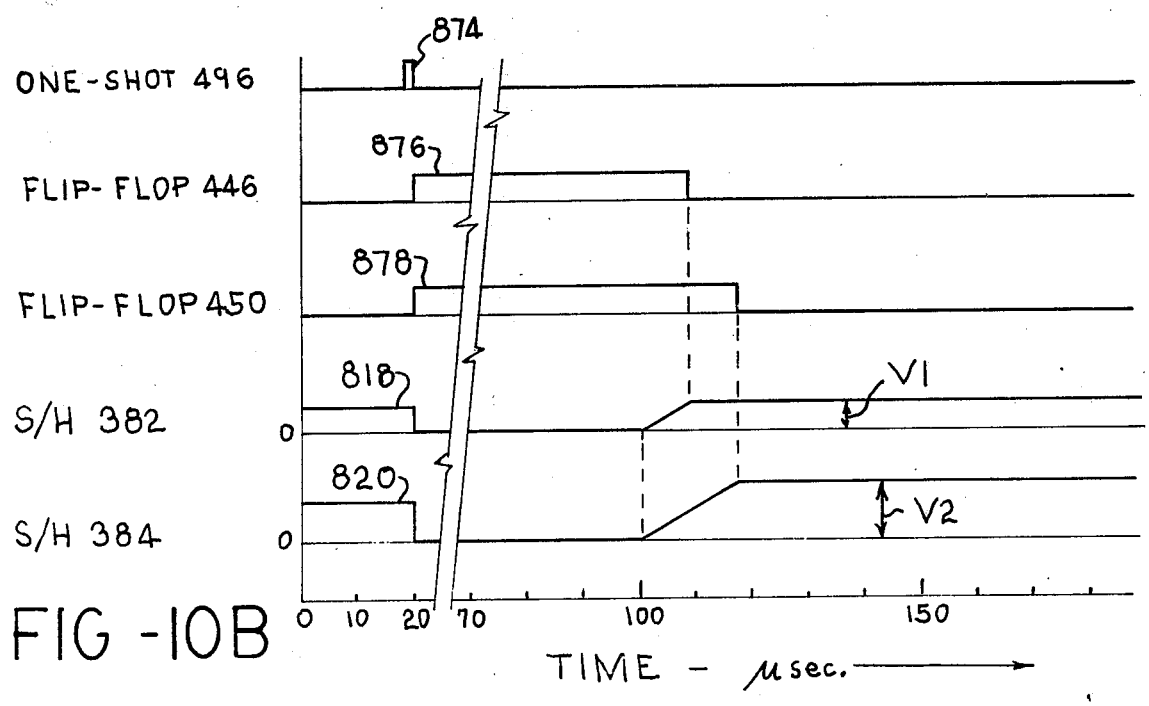

Vertical deflection signals for Doppler display are provided by a ramp signal generator 380 in conjunction with outputs from sample and hold circuits 382 and 384, all of which are shown in FIG. 1D. As seen in the displays of FIGS. 3 and 4, both the Doppler profile 68 and cursor 70 are displayed between the same vertical deflection levels and consequently, the ramp signal for vertical deflection during Doppler display is required to operate only between such levels. Once each B-scan frame the Doppler and B-scan transmitters are simultaneously operated, and the sample and hold circuits 382 and 384 subsequently are controlled to sample and hold the B-scan deflection signal present at the beginning and end, respectively, of the Doppler signal storage sequence executed by the sample and hold circuits 330-1 through 330-20 (FIG. 1C). The output signals 818 and 820 from the sample and hold circuits 382 and 384, respectively, are shown in FIGS. 9 and 10B and the means for controlling the sample and hold circuits 382 and 384 are described below. For present purposes it will be understood that the sample and hold circuit outputs 818 and 820 are established at the required levels, identified as V1 and V2, once every B-scan frame and remain thereat during the remainder of the B-scan cycle for use in controlling the rate of operation of the commutator 346 and for use in generating Doppler vertical deflection signals.

As described above, a Doppler display sequence is initiated with an output 756 (FIG. 7) from the comparator 224 (FIG. 1B) which output conditions the multiplexer 156 for Doppler transmission, through use of the logic network 190, and which also triggers the one-shot 226. The one-shot 226 output 822 (FIG. 9) is supplied over line 228 (from FIG. 1B to FIG. 1D) as a clock input to a flip-flop 388. The $\overline{Q}$ output terminal of flip-flop 388 is connected to the data terminal for toggle operation of the flip-flop. A Doppler signal profile display is initiated when the Q output terminal switches to a low level, and a Doppler cursor display is initiated when the Q output terminal switches high. It will be apparent then that a Doppler profile is displayed on alternate outputs from the comparator 224.

DOPPLER PROFILE - X-AXIS

Assume, now, that the Q output from the flip-flop 388 switches from high to low to initiate a Doppler profile display. The flip-flop 388 output 824 is supplied as the data input to a flip-flop 390, to which clock pulses are supplied from a voltage controlled oscillator (VCO) 392. The flip-flop 390 thereby also switches states upon receipt of a clock pulse from the VCO 392 following a change in state of the input to the D terminal. The falling edge of the flip-flop 390 output 826 at output terminal Q triggers a one-shot 391 having an output pulse 828. The pulse 828 from the one-shot 391 is supplied as a reset signal to counter 350 to reset the same, and is connected through an OR gate 394 to the control input of the ramp generator 380 to trigger on the same. The $\overline{Q}$ terminal output from the flip-flop 390 is connected as one input to an AND gate 396 to enable the same for passage of clock pulses from the VCO 392 therethrough. The clock pulses 830 from the AND gate 396 clock the counter 350 and, as described above, the commutator 346 (FIG. 1C) switches under control of signals from the counter 350 for passage of the Doppler profile signals from the frequency to voltage converters 344-1 through 344-20 to the horizontal deflection circuit of the cathode ray tube 66. The VCO 392 frequency is controlled by the voltage output from a difference amplifier 398 having input signals V1 and V2 supplied thereto from the sample and hold circuits 382 and 384, respectively. Consequently, the clock rate is determined by the difference in the voltages V1 and V2, with the output frequency of the clock decreasing with an increase in the voltage difference between V1 and V2. It will be seen, then, that the rate at which the counter 350 is clocked, and the commutator 346 is stepped, is inversely proportional to the difference between the voltages V1 and V2.

Although the AND gate 396 remains enabled for passage of clock pulses from the VCO 392 until the flip-flop 390 changes state, it will be apparent that only the first twenty (20) clock pulses are employed by the counter 350 for stepping the commutator 346 to read out the analog Doppler profile signals from the twenty (20) frequency to voltage converters. In FIG. 9, the first, twenty clock pulses are shown produced between times T6 and T7. For proper display of these signals, a vertical deflection signal must be supplied to the cathode ray tube which signal ramps between the V1 and V2 levels between the times T6 and T7.

DOPPLER PROFILE - Y-AXIS

A vertical ramp signal, for both Doppler profile and Doppler cursor display, is supplied to the multiplexer section 156Y over line 410 from an amplifier 402 (FIG. 1D to FIG. 1B). The amplifier 402 and its associated input and feedback resistors comprise a summing circuit for summing the input potentials supplied thereto. The amplifier 402 is provided with a first input V1 from the sample and hold circuit 382. A second input for the amplifier is supplied from either the ramp generator 380 or sample and hold circuit 384, depending upon the condition of transmission gates 400 and 402 connecting the ramp generator and sample and hold circuit outputs to the amplifier input. The ramp generator 380 and sample and hold 384 outputs 831 and 820, respectively alternately are supplied to the amplifier 402 by operating the transmission gates 400 and 404 in such a manner that one is enabled while the other is disabled. Control signals for the gates 400 and 404 are obtained from a comparator 406. The output from the comparator is directly connected to the gate 400, and is connected through an inverter 408 to the other gate such that when one gate is enabled the other gate is disabled. Comparator inputs are provided by the ramp generator 380 and sample and hold circuit 384 outputs.

In operation, as described above, the ramp generator 380 is gated on by the output 828 (FIG. 9) from the one-shot 391 connected thereto through the OR gate 394 at the same time that the AND gate 396 is enabled for passage of VCO output clock pulse 830 therethrough. When the generator 380 is enabled, the ramp signal output 831 therefrom rises from a zero level. Upon reaching the level of the signal output 820 from the sample and hold circuit 384, at V2, the comparator 406 produces an output 832 which switches the transmission gates 400 and 404 to disable the gate 400 and to enable the gate 404. Now, the signal output V2 from the sample and hold circuit 384 is supplied as a second input to the amplifier 402, rather than the ramp signal generator 380 output. With the use of proper scaling resistors at the inputs to the amplifier 402 the output 834 therefrom (FIG. 9) ramps between voltage levels V1 and V2 between times T6 and T7 during which the commutator 346 (FIG. 1C) is being stepped to read the Doppler profile information from the frequency to voltage converters 344-1 through 344-20 out to the X-axis input to the cathode ray tube 66 through the amplifier 356.

DOPPLER Z-AXIS

Z-axis control during Doppler profile and cursor displays is provided by square wave outputs from ramp generator 380 and a ramp generator 418 (for cursor generation, described below) which square wave outputs are connected through an OR gate 411 and over line 413 (FIG. 1D to FIG. 1B) to the Doppler Z-axis input to the multiplexer 156 for connection to the control grid 158 of the cathode ray tube 66.

CURSOR GENERATION

As noted above, the Doppler profile and cursor signals are supplied to the cathode ray tube on alternate Doppler display periods. The flip-flop 388 is triggered by the output 822 from the one-shot 226, and a Doppler profile signal is displayed when the Q output thereof switches from high to low, in the manner described above. (See FIG. 9). When the flip-flop 388 is next triggered by the one-shot output 822, and the output therefrom goes from low to high, a Doppler cursor signal is generated and displayed at the cathode ray tube 66. The rising edge of waveform 824 from flip-flop 388 triggers a one-shot 414, and the output pulse 836 therefrom (FIG. 9) is connected through an OR gate 416 to a ramp generator 418 to trigger the same. The ramp signal generator 418 is used in the generation of the horizontal end sections 70A and 70B of the Doppler cursor. The generator 418 has both ramp 838 and square wave 840 outputs which are produced when the generator is triggered by the one-shot 414. The ramp signal output is connected through a first transmission gate 420 to the summing junction J to the amplifier 356 (FIG. 1C) over line 360. A DC potential, from a DC source and potentiometer 422, (FIG. 1D) is connected to the summing junction through a second transmission gate 424. The potentiometer 422 is adjusted to provide a DC potential to the gate 424 which is substantially equal to the midpoint potential of the ramp signal 838, for reasons which will become apparent hereinbelow.

The gates 420 and 424 are gated on and off by use of the squarewave output 840 from the ramp generator, with the squarewave gating signal being supplied to the gate 420 through an inverter 426 so that the one gate is enabled while the other gate is disabled. In FIG. 9, the outputs from the gates 420 and 424 are identified by the reference numerals 842 and 844, respectively. The gate 424 normally is enabled for connection of the constant DC potential therethrough to the amplifier 356. The DC potential from the gate 424 essentially adds a constant DC value to the horizontal position control signal supplied to the amplifier 356 from the control unit 44 (FIG. 1C). When the ramp signal generator 418 is enabled, the square wave output therefrom disables transmission gate 424, for removal of the DC source therefrom, and enables transmission gate 420, for connecting of the ramp signal therethrough. The combined outputs from gates 420 and 424, identified by reference numeral 846 in FIG. 9, includes first and second offset ramp sections 846A and 846B for generation of the cursor end sections 70A and 70B, respectively. The second end section 70B is generated following generation of a vertical ramp signal for the vertical portion of the cursor 70 in a manner now to be described.

The trailing edge of the squarewave 840 from the generator 418, at time T 12, triggers a one-shot 428, and the output 848 from the one-shot is connected through the OR gate 394 to the ramp generator 380 to enable the same. The operation of the ramp generator 380 and sample and hold circuits 382 and 384 in the generation of the vertical deflection signal 834 for Doppler profile display was described above. Here the ramp generator is gated on by the pulse output 848 from the one-shot 428 rather than by the pulse output 828 from the one-shot 391. As described above, when the ramp signal 831 from ramp generator 380 reaches the level V2 from the sample and hold circuit 384, an output 832 is produced by the comparator 405 which is used to switch the transmission gates 400 and 404. It here will be noted that the comparator output 832 also is connected to a one-shot 430 to trigger the same. The one-shot 430 output 850 is connected to the ramp generator 418 through the OR gate 416 to enable the same. The lower cursor end signal, designated 846B is thereby produced at the combined outputs from the transmission gates 420 and 424, in the manner described above, for generation of the cursor end 70B.

ESTABLISHING DOPPLER VERTICAL SCAN LEVELS

Periodically, the sample and hold circuits 382 and 384 are operated to establish and to periodically update the V1 and V2 signal levels, respectively, necessitated, for example, by initial turn-on of the equipment, by changes in the Doppler length and/or vertical settings of the control stick 48, by decay in the output voltage of the sample and hold circuits with time in the hold mode, and the like. It will be apparent that the voltage levels V1 and V2 from the sample and hold circuits 382 and 384 must identify the levels from which the first and last Doppler echo signal stored by the sample and hold circuits 330-1 and 330-20 are acquired for proper display of the stored Doppler profile signals. The B-scan vertical deflection signal, in timing and slope, is correct, of course, for proper display of the B-scan signals. With the present arrangement, the B-scan and Doppler transmitters periodically are simultaneously operated and, with the B-scan vertical deflection signal supplied as an input to the sample and hold circuits 382 and 384, the deflection signal is sampled by the sample and hold circuits 382 and 384 at the instants that the first and last Doppler signal are stored by the respective sample and hold circuits 330-1 and 330-20. In the illustrated arrangement the first timing pulse from the photocell 104 generated each frame is used to control the B-scan and Doppler units for the simultaneous generation of ultrasonic pulses by the B-scan and Doppler transducers 20 and 22. The timing means for effecting the simultaneous B-scan and Doppler transmitting operations includes a flip-flop 480 shown in FIG. 1D. The R terminal input of the flip-flop 480 is connected to the output from a one-shot 482 which, in turn is triggered by the photocell 104 output connected thereto over line 484 from FIG. 1A to FIG. 1D through FIG. 1C. Output pulses from the one-shot 482 therefore are produced at the same sinusoidally varying rate as photocell 104 pulses 602 shown in FIG. 10A. The S input terminal of the flip-flop 480 is connected to the output 866 from the one-shot 162 over line 486 from FIG. 1A through FIG. 1C to FIG. 1D. The one-shot 162 is triggered once per cycle of the output 604 from the photocell 106 at one end of the B-scan sweep to set the flip-flop 480. A reset signal occurs a short time later, upon occurrence of the first fast timing pulse from the photocell 104, to reset the flip-flop. In FIG. 10A the flip-flop 480 output is identified by the reference numeral 868. Other fast timing pulses from the photocell 104 have no effect upon the operation of the flip-flop 480 until the flip-flop is again set at the beginning of the next B-scan cycle.

The trailing edge of the flip-flop output 868, which corresponds in time to the first timing pulse from the photocell 104, is used to trigger a one-shot 488 which, in turn, sets a flip-flop 490. The flip-flop 490 output 870 is connected as one input to an AND gate 492. The other AND gate input comprises the Doppler transmit/receive control pulse 802 from one-shot 294 connected thereto over line 494 from FIG. 1C to FIG. 1D. The Doppler system may operate at a repetition rate of, say 10,000 pulses per second, and only approximately 1/30 of the transmit/receiver control pulses 802 are shown for clarity in FIG. 10A. The gated signal 872 from AND gate 492 triggers a one-shot 496, the inverted signal output from which is connected as a reset signal to the flip-flop 490 to reset the same in preparation for the next output pulse from the one-shot 488. The other one-shot 496 output 874 is used to trigger operation of the B-scan system for simultaneous operation thereof with the Doppler system. To this end the output 874 is connected through lead 498 (from FIG. 1D to FIG. 1A through FIG. 1C) and through the OR gate 140 and delay units 174 and 176 to the ramp signal generators 178 and 180. As described above, the ramp generator outputs are employed as vertical deflection signals for the B-scan display, and the selected ramp generator output is obtained at line 184 from the transmission gate 182.

With the Doppler system operating at a pulse repetition rate of 10,000 pulses per second, it will be understood that a delay of up to 100 microseconds may exist between the triggering of the one-shot 496 (upon occurrence of the first B-scan timing signal from the photocell 104) and the triggering of the B-scan system. Because of such improper timing the first line of B-scan information is not displayed. Display of this line of information at the cathode ray tube 66 is prevented by any suitable means. In the illustrated arrangement, the gain function generator 138 is disabled to disable operation of the time variable gain amplifier 136 at this time. To this end the signal 874 from the one-shot 496 is connected to a delay unit 502 (FIG. 1A) such as a one-shot, having an output with a pulse period which exceeds the period of the pulses from the delay units 174 and 176. The one-shot 502 output is connected through an inverter circuit 504 to the AND gate 141 to keep the output therefrom low during the presence of the output pulse from the delay unit 174 thereby preventing triggering operation of the gain function generator 138. Without triggering the gain function generator, the amplifier 136 remains disabled and no B-scan line of information is obtained from the compression amplifier 154 at the B-scan receiver output. Also, means not shown may be used to prevent triggering of the pulser 126 at this time to avoid transmission of a B-scan pulse.

The vertical deflection signal for B-scan operation at line 184 from the transmission gate 182 is supplied over line 436 from FIG. 1A to FIG. 1D through FIG. 1B, as an analog input signal to the sample and hold circuits 382 and 384. Control signals are supplied to the sample and hold circuits 382 and 384 for momentarily switching the same to the sampling mode from the hold mode when the first and last sample and hold circuits 330-1 and 330-20 respectively, (FIG. 1C) are actuated during Doppler receiver operation. In the illustrated arrangement the control signals are obtained by use of the clock signals 814 (FIG. 8) from the programmable frequency clock 340 (FIG. 1C). The clock signals, in addition to clocking the shift register 334, are connected over line 442 to a counter 444. The counter may comprise, for example, a pair of binary coded decimal up counters connected in cascade in the ripple mode. The "1" output terminal of the counter is supplied as a reset signal to a flip-flop 446. The "4" and "16" output terminals are connected to the input of an AND gate 448 to provide an output therefrom at the count of "20", which output is used to reset a second flip-flop 450. The counter 444 is reset and the flip-flops 446 and 450 are set by the pulse output 874 from the one-shot 496 once every B-scan frame immediately prior to above-described counting operation of the counter 444 and resetting of the flip-flop 446 and 450. The flip-flop 446 and 450 outputs designated 876 and 878, respectively are shown in FIG. 10B. These flip-flop outputs are supplied as control signals to the sample and hold circuits 382 and 384 for switching the same to the sample, or tracking, mode while the flip-flops are in the set condition. Consequently, it will be seen that the B-scan vertical deflection signal supplied as an input to the sample and hold circuits 382 and 384 is sampled and held at the beginning and at the end of the acquisition of the Doppler profile signal. The outputs from the sample and hold circuits 382 and 384 during such periodic updating thereof are identified by reference numerals 818 and 820, respectively, in FIG. 10B. The signal levels V1 and V2 held by the sample and hold circuits 382 and 384 are used both in the generation of the cursor 70 to set the end levels thereof and, in the display of the Doppler profile 68 to set the vertical end levels and to establish the rate at which the individual segments thereof are displayed, in the manner described above.

RETICLE SIGNAL GENERATOR

An electronic reticle signal generator 510, shown in FIG. 1B, is included to provide calibrated tick marks along the margins of the display for use in tissue metrology, and the like. As mentioned above, and as seen in FIGS. 2 and 3, tick marks for the 1X operation are identified by the reference characters 80-1 through 80-60, respectively. For the 2X display, as shown in FIG. 4, the tick marks are identified by the reference characters 82-1 through 82-28. Also as described above, 2X field indicator marks 83-1 through 83-4, as seen in FIG. 3, may be provided with the 1X display to indicate the 2X boundries when switching from the 1X to the 2X display. In FIG. 5, the reticle on-off and 2X field indicator switches 92 and 94, respectively, are shown.

Referring to FIG. 1B, the reticle signal generator 510 is shown comprising a decoder 512 comprising, for example, eight 4 lines to 1 decoders. The decoders are provided with some hard-wired inputs and some switchable inputs through the 1X, 2X switch section 90-1 and 2X field indicator switch 94. The switches 90-1 and 94 are shown comprising single pole double throw switches, each with one terminal connected to a high level input and the other connected to a low level input. The output from switch 90-1 is connected as an input to selected decoder input terminals and to an AND gate 514. The output from the 2X field indicator switch 94 provides a second input to the gate 514. In the illustrated arrangement, for purposes of description only, decoder binary outputs of 0, 64, and 128 are provided with switch 90-1 and 94 settings of 1X, 2X and 1X with 2X field indicator, respectively.

The decoder 512 outputs are supplied as input signals to a presettable counter 516, whereby the counter is preset to the count provided from the decoder 512 output upon receipt of a load signal from the one-shot 214. The one-shot 214 is triggered whenever a signal input thereto is provided from the comparator 212, in the manner described above, whenever a reticle cycle is to be performed. It will be understood then, that with the switch 90-1 in the 1X position and the switch 94 open, the counter 516 is loaded with a count of zero upon receipt of a load signal thereto; that with the switch 90-1 in the 2X position, the counter 516 is loaded with a count of sixty four (64) when the load terminal is energized; and that with the switch 90-1 in the 1X position and the switch 94 in the closed position, the counter 516 is loaded with a count of 128 when the enable terminal is energized. As is understood, upon receipt of clock pulses at the clock input to the counter counting proceeds from the preselected, or preloaded, value of zero, sixty four or one hundred twenty eight, in the illustrated arrangement.

The one-shot 214 output 900 (FIG. 11) for loading of the counter 516 also is supplied to a delay unit 518 comprising, for example, a one-shot having an output 902. As described above, the comparator 212 output, through the logic network 190, is used for multiplexer channel control to switch the multiplexer 156 for reticle display. The delay provided by the one-shot 518 allows for settling of the multiplexer 156 before transmission of reticle signals therethrough after switching channels.

The one-shot 518 output 902 is connected to the reset terminal of a flip-flop 520 which is reset to the trailing edge thereof. The flip-flop 520 output 904 serves as a gating signal which is connected to a free running clock 522 for on-off control thereof. The clock output 906 is connected both to the input of the counter 516 to drive the same, and through a NOR gate 523 to the input of a delay unit 524 to trigger the same. The reticle on-off control switch 92 is shown included in the DC supply circuit for the delay unit 524 for on-off control of the reticle generator. Other locations for such on-off control of the reticle generator will be apparent. In FIG. 11, the one-shot 524 output is identified by the reference numeral 907.

The contents of the counter 516 are supplied to a programmable read only memory (PROM) 526 having first and second outputs (Y-out and X-out) which, in turn, are connected as inputs to digital to analog. (D/A) converters 528 and 530. The analog outputs 908 and 910 from the D/A converters 528 and 530 are connected through the multiplexer 156 to the respective vertical and horizontal deflection circuits of the cathode ray tube 66 for positioning of the tick marks at the face of the screen. After the counter 516 is stepped, the delayed clock pulse from the above-mentioned delay unit 524 triggers a one-shot 532 having an output which is connected through the multiplexer 156 to the control grid of the cathode ray tube 66 for on-off Z-axis control thereof. The delay provided by delay unit 524 allows for settling of the vertical and horizontal deflection voltages from the D/A converters 528 and 530 before the Z-axis is turned on, or enabled, by the output of the one-shot 532. With the present arrangement the PROM 526, in effect, converts the counter 516 output to digital number representations of the Y and X axis coordinates of reticle tick marks, which digital signals then are converted by the D/A converters 528 and 530 to analog vertical and horizontal deflection signals for the cathode ray tube.

At the end of the reticle display (e.g. at count 61 of the counter 516 for 1X display, at count 93 for 2X display, and at count 193 for 1X with 2X field indication display), the PROM 526 is programmed to provide the same output. This PROM output is decoded by a decoder 533, and the decoder output 912 is supplied to the flip-flop 520 to set the same, thereby stopping the clock 522. The decoder output also is applied to the reset terminal of the one-shot 532 to prevent output pulses therefrom. It will be seen, then, that when the counter 516 is clocked by the final clock pulse in the cycle, no Z-axis signal is supplied to the cathode ray tube since the one-shot 532 is disabled before the delayed clock pulse reaches the same. The reticle generator remains in this quiescent condition until actuated by another pulse from the one-shot 214 when an output is provided from the comparator.

For convenience in use of the reticle, the spacing between adjacent tick marks identifies the same distance for both 1X and 2X operating conditions which, in the illustrated arrangement, comprises a distance of 2 millimeters. It will be seen, then, that substantially twice as many tick marks are required for 1X operation as for 2X operation. Since the clock 340 operates at the same rate for both 1X and 2X operation, a reticle cycle of a display of the tick marks for 2X operation requires approximately one-half the time required for the 1X reticle display. A somewhat longer period is required where the 2X field indicator is included with the 1X display.

OPERATION

Although the operation of the ultrasonic B-scan/-Doppler imaging system is believed to be apparent from the above description, a brief description thereof with reference to the waveforms of FIGS. 6 through 11 now is given. As the motor 40 drives the focused broadband B-scan transducer 20 back and forth across the subject 26 at a generally sinusoidally varying rate (FIG. 6, waveform 600), timing pulses 602 are produced by the photocell 104, which pulses occur at the sinusoidally varying rate of movement of the transducer. During such scanning operation, a symmetrical squarewave 604 is produced at the photocell 106 output which switches signal levels at opposite ends of the transducer 22 travel.

The fast and slow master timing signals 602 and 604 are used to control B-scan transmitting and receiving operations. For 1X operation the fast master timing signal 602 is divided by a divide-by-two circuit 108 (FIG. 1A) and supplied through gate 110 to the pulser 126. Impulses from the pulser are supplied to the transducer 20, and the resultant short, focused, ultrasonic pulses travel into the subject to be reflected from internal discontinuities therewithin. For the 1X operation an area 85-1X (FIG. 1A) is scanned, which area lies along the transducer axis 30. Both the B-scan and Doppler transducers 20 and 22 are focused at substantially the midpoint depth of the imaged area.

The B-scan receiver is recurrently operated, following B-scan pulse transmission, for the reception of echo signals received between the upper and lower levels of the section imaged, and the simultaneous display thereof. To this end, the master timing pulse output from the divide-by-two circuit 108 is delayed by delay unit 174, and subsequently triggers operation of the receiver gain function generator 138 and a vertical ramp signal generator 178. The ramp signal 708 from generator 178, for 1X operation is connected through multiplexer section 156Y to the vertical deflection circuit of the cathode ray tube 66 for vertical deflection in an amount dependent upon the time lapsed from the preceding transmitter pulse. The generator 178 also includes a squarewave output 712 which, through logic network 190, is connected as a channel control signal to the multiplexer for passage of B-scan signals therethrough. The B-scan display at the cathode ray tube 66 is intensity modulated by connection of the B-scan receiver output from compression amplifier 154, through line 155 and multiplexer 156, to the control grid thereof. The X axis deflection signal for the B-scan display, which is proportional to the transducer 20 position, is provided by use of a master up-down counter 160 to which the fast master timing signals 602 are supplied to step the same, and to which the slow master timing signals 604 are supplied for up-down control. The digital count output is converted by a digital to analog converter 168 to analog form 620-1 for connection to the horizontal deflection circuit of the cathode ray tube through the multiplexer. It will be seen, then, that the B-scan signals from the B-scan receiver are displayed as they become available at the receiver output at a rate dependent upon the master timing pulses from the divide-by-two circuit 108, with 1X operation.

For 2X B-scan display, only the master timing pulses produced during the central portion of the B-scan transducer 20 sweep are employed. Those pulses produced at the opposite ends of the sweep, during travel along the initial and final quarters of the path length, are blocked and, therefore, do not function to trigger the pulser 126 or the delay unit 176. The circuit for passing only the master timing pulses generated during the central portion of the B-scan sweep includes an up-down counter 118 which is stepped by the master timing pulses 602 from the photocell 104. Up-down counter control is provided by the slow clock pulse 604. Decoders 120-1 and 120-2, responsive to the count from the counter 118 provide outputs 612-1 and 612-2 when the count passes 101 and 300, respectively. Logic means 121, responsive to the decoder outputs 612-1 and 612-2, in effect, serves to pass master counter pulses to trigger the B-scan transmitter between the counts at which the decoders 120-1 and 120-2 are designed to operate. The pulse output 608 from the logic network 121 triggers the pulser 126 to produce a transmitter pulse, and triggers a 2X delay unit 176 for delay triggering of the 2X ramp generator 180. The ramp generator output 710 rises at twice the rate of the 1X ramp generator output 708 to vertically sweep the cathode ray tube electron beam the same vertical distance but in substantially one-half the time required for 1X display. (As noted above, a single ramp generator may be employed, with the generator output amplified by different amounts to provide for the different ramp signal slopes.) The timing pulses 608 also are supplied to the master counter 160 for generation of the stepped horizontal deflection signal 620-2 from the D/A converter 168 in the same manner described above for 1X operation. Both the horizontal and vertical deflection signals for 2X display operate between the same levels as the horizontal and vertical deflection signals for 1X display, but change at substantially twice the rate, for display of the imaged section 85-2X over the same screen area as the 1X display. In this manner an enlarged view of the central portion of the 1X display is provided. There is no appreciable change in picture quality in switching between 1X to the 2X operating modes since the display is made up of the same number of lines for both the 1X and 2X operating conditions.

Except for the one timing pulse per B-scan frame used in the establishment of the upper and lower levels for the Doppler vertical deflection signal, the above-described B-scan transmit, receive, and display operations take place independently of the Doppler system operation. Also, the Doppler transmit and receive operations are performed asynchronously with respect to the B-scan operation. Doppler display, as well as reticle generation and display, on the other hand, are timed for execution between selected B-scan displays. In particular, they are executed adjacent the opposite ends of the B-scan where the operating rate is a minimum.

The Doppler transmit and receive operations include the use of the clock signal 800 (FIG. 8) for producing a pulse 802 for periodically conditioning the T/R switch 298 for a transmit operation and for producing another slightly delayed pulse 806 for enabling the RF transmission gate 308. Phase-coherent 5MHz bursts 880 (FIG. 8A) from the RF signal generator 310 and gate 308 are amplified by power amplifier 312 and delivered to the Doppler transducer 22 through the T/R switch 298. Received signals 882, including signals reflected from moving interfaces and particles within the subject 26, are connected as one input to a demodulator 322 through the T/R switch 298, the preamplifier 318, and the amplifier 320. An offset frequency version of the RF signal generator 310 output is supplied as a second input to the demodulator. The amplitude of the demodulator output signal 884 at any given time in the Doppler return is proportional to the phase (relative to the second input signal) of the waves reflected from a small volume (e.g. one-cubic millimeter volume) of the subject at a proportional distance from the transducer; the volume being related to the pulse length and the focusing, or collimation, of the transmitted acoustic wave. For return signals from particles or interfaces having a component of movement along the transducer axis 30, the relative phase changes with time. For stationary objects, the relative phase is unchanged with time.

The signal 884 from the demodulator 322 is sequentially sampled by the sample and hold circuits 330-1 through 330-20. The sampled voltages held by the sample and hold circuits are proportional to the signal phase at successive points along the transducer axis 32. The sampling is effected by use of the gateable clock 340, the output from which is used to clock a shift register 334 which, in time, sequentially operates the sample and hold circuits. The clock 340 is gated on, i.e. enabled by the output from voltage controlled delay unit 336, with the delay being adjusted by the vertical output from the control stick unit 44 as determined by the vertical setting of the control stick. The clock rate is established by the length control output of the control stick 44 which controls the length of the Doppler axis 30 along which the return signals are sampled. The position of the Doppler transducer 22 along its path of travel is adjustably set by the horizontal, or X-axis, output from the control stick unit. Complete one hand control of the line along which the Doppler return signals are obtained is provided with this arrangement.

The sample and hold outputs 886 (FIG. 8B) are filtered by notch filters 332-1 through 332-20 to substantially, but not completely, remove therefrom the difference frequency signal (fo), produced at the output of demodulator 322. Sample and hold switching transients also are removed. The signals 888 from the notch filters are converted to equivalent analog signals 890 representative of the Doppler signal frequency by frequency to voltage converters 344-1 through 344-20. The frequency to voltage converters are of the zero crossing type which include low pass filters in the output circuits thereof for maintenance of levels between zero crossings of the input signals.

The analog Doppler signal levels from the frequency to voltage converters 344-1 through 344-20 are displayed between pre-established B-scan line displays; the Doppler profile and the Doppler cursor signals being displayed on alternate Doppler display periods. Timing for Doppler display is provided by the output 756 (FIG. 7) from the logical comparator 224 (FIG. 1B). The master up-down counter 160 (FIG. 1A), having an output indicative of the B-scan line, provides one input to the comparator. A second comparator input is provided by the output from the PROM 222. With equal logical inputs thereto, an output is obtained therefrom which is used to trigger the Doppler display. Address select signals for the PROM are supplied from the Doppler counter 220, which is stepped by the comparator output. The PROM is programmed to provide outputs which will result in comparator outputs between selected B-scan lines.

The comparator 224 output 756 (FIG. 7) through logic network 190, conditions the multiplexer 156 for Doppler channel transmission. The comparator output also triggers the one-shot 226 which, in turn, triggers the toggled flip-flop 388 (FIG. 1D) having an output 824 (FIG. 9). When the flip-flop 388 is toggled high the Doppler cursor 70 is displayed, and when toggled low, the Doppler profile 68 is displayed. The low output signal from the Q terminal of the flip-flop 388 is applied to the data input terminal of the flip-flop 390 which then changes state upon receipt of the first clock pulse to arrive thereat from the VCO 392. The $\overline{Q}$ output from the flip-flop, now high, enables the AND gate 396 for passage of clock pulses from the VCO 392 therethrough to the counter 350. The counter 350 is connected over line 352 to the commutator 346 which sequentially samples the outputs 890 from the frequency to voltage converters 344-1 through 344-20. The commutator output, comprising the Doppler profile signal, is connected through the amplifier 356, the amplifier 364 for 2X operation or the gate 366 for 1X operation, and the multiplexer 156, to the horizontal deflection circuit of the cathode ray tube 66 for Doppler profile display.

The ramp vertical deflection signal for Doppler display operates between upper and lower deflection voltage limits related to the timing of the initiation and termination of the sample and hold functions of the sample and hold circuits 330-1 through 330-20 during Doppler receiver operation. The upper and lower deflection voltage limits for Doppler display are established recurrently (i.e., once each B-scan frame) by the simultaneous actuation of the B-scan and Doppler systems. The signal for such simultaneous actuation is produced by setting the flip-flop 480 (FIG. 1D) by the output 866 (FIG. 10A) from the one-shot 162 which, in turn, is triggered once each B-scan frame by the photocell 106 output 604. The flip-flop 480 is reset by the first fast clock pulse 602 to occur at the beginning of the B-scan frame, and the trailing edge of flip-flop 480 output 868 triggers a one-shot 488 which, in turn, sets the flip-flop 490. The flip-flop 490 output 870 enables the gate 492 for passage of a signal from the one-shot 294 which is triggered by the Doppler clock 292. The one-shot output signal 872 from the AND gate 492 triggers a one-shot 496 which resets the flip-flop 490 and triggers operation of the 1X and 2X delay circuits 174 and 176 included in the B-scan receiver. The trailing edge of the pulse outputs from the delay units 174 and 176 trigger ramp generators 178 and 180, and the selected ramp signal output, depending upon the setting of gate 182 (FIG. 1A), is connected to the input terminals of sample and hold circuits 382 and 384 over line 184 from FIG. 1A to FIG. 1B, and line 436 from FIG. 1B to FIG. 1D.

The ramp signal inputs are sampled at the beginning and end of the Doppler receiver storage operation, when sample and hold circuits 330-1 and 330-20, respectively, are operated to sample the Doppler signal. To this end, control signals for the sample and hold circuits 382 and 384 are obtained from the clock 340 output 814 (FIG. 8) which drives the counter 444. At the counts of 1 and 20, outputs from the counter reset flip-flops 446 and 450 having outputs which control the sample and hold circuits 382 and 384, respectively. The sample and hold outputs 818 and 820 (FIG. 9) identify the vertical levels between which the Doppler profile signals are acquired during Doppler receiver operation.

Vertical deflection for the Doppler profile display now is described. The $\overline{Q}$ output of flip-flop 390 enables gate 396 for passage of clock pulses from the VCO 392 to the counter, in the manner described above, for stepping the same and actuating the commutator 346. The Q output 826 (FIG. 9) of the flip-flop 390 triggers the one-shot 391, and the one-shot output 828 is connected to the ramp generator 380 through OR gate 394 to trigger operation thereof. The ramp signal output 831 is connected through the transmission gate 400 to the input of the amplifier 402, together with the sample and hold 382 output V1. The amplifier output 834 is connected through the multiplexer 156 to the vertical deflection circuit of the cathode ray tube 66. When the vertical deflection signal from the ramp generator 380 reaches the level of V2 from the sample and hold circuit 382, an output 832 is produced from the comparator 406 which opens (disables) the gate 400 and closes (enables) the gate 404, connecting the sample and hold 384 output V2 to the amplifier. The VCO 392 operating frequency is controlled by the difference between the outputs V2 and V1 from the sample and hold circuits 384 and 382 through use of difference amplifier 398 in a manner such that the commutator 346 is operated at the proper rate to read out the values from the frequency to voltage converters 344-1 through 344-20 while the vertical deflection signal ramps from the V1 to the V2 level. Z-axis control for the Doppler display is provided by the output at line 413 from gate 411 connected to the cathode ray tube 66 through the multiplexer 156.

When the flip-flop 388 is next toggled by an output 822 (FIG. 9) from the one-shot 226 (which is triggered by the comparator output in the manner described above) the Doppler cursor 70 is displayed. The leading edge of the Q output 824 from flip-flop 388 triggers the one-shot 414, and the one-shot 414 output (836) through OR gate 416, triggers operation of the ramp generator 418. The ramp signal output 838 from the ramp generator is connected as an input to the transmission gate 420. The ramp generator also has a square wave output 840 comprising a control signal for the gate 420 and, a second transmission gate 424, which are switched in a manner such that one gate is closed while the other is open. The input to the gate 424 comprises a DC potential at a level which is intermediate the end levels of the ramp signal from the generator 418. The gate 424 normally is closed (enabled) for connection of such DC potential to the input to the amplifier 356. As described above, the amplifier 356 output is connected through amplifier 364 or gate 366 to the horizontal deflection circuit of the cathode ray tube through the multiplexer 156 during Doppler display. The DC signal from the gate 424 together with the horizontal signal from the control stick unit 44 which also is connected to the amplifier 356, establish the X-axis position of the cursor 70 and reference for the Doppler profile display. The ramp signal output 838 from the generator 418 when connected to the amplifier 356 during ramp generation functions to horizontally sweep the electron beam of the cathode ray tube 66 to opposite sides of the normal position for generation of the end mark 70A.

The trailing edge of the squarewave output 840 (FIG. 9) from the ramp signal generator 418 triggers a one-shot 428. The one-shot output 848, through OR gate 394, triggers operation of the ramp generator 380 which, as described above, provides for a ramp signal 831 at the transmission gate 400 output which extends between the V1 and V2 levels supplied by the respective sample and hold circuits 382 and 384. When the ramp signal output 831 reaches the V2 level from the sample and hold circuit 384, the comparator 406 operates (output 832) to trigger the one-shot 430. The one-shot output 850 is connected through OR gate 416 to the ramp generator 418 for generation of the lower cursor end mark 70B (FIGS. 3 and 4). When the flip-flop 388 is next toggled the Doppler profile is displayed in the manner described above, for the alternate display of Doppler profile and cursor signals, depending upon which direction flip-flop 388 is toggled. With the present arrangement proper registration of the Doppler and B-scan displays is assured by the above-described periodic simultaneous operation of the B-scan and Doppler receiver systems for updating the V1 and V2 levels held by the sample and hold circuits 382 and 384.

Reticle generation and display, when switched on by closure of switch 92, is provided between other selected B-scan lines as determined by the contents of PROM 210. The reticle counter 204, RPOM 210, comparator 212 and one-shot 214 are similar to and operate in a manner similar to the above described operation of the Doppler counter 220, PROM 222, comparator 224 and one-shot 226, and such operation is not repeated here. An output from the comparator 212 sets the flip-flop 254 in the logic network 190, the output from which flip-flop is supplied as a gate enable signal to gate 256. The trailing edge of the square wave output 712 (FIG. 7) from 1X of 2X ramp generator 178 or 180, depending upon the setting of gate 182, triggers the one-shot 242 in the logic network 190, and the one-shot output 752 is transmitted through the enabled gate 256 to set the flip-flop 258 for reticle channel control of the multiplexer 156.

The reticle comparator 212 output also triggers the one-shot 214 the output 900 (FIG. 11) from which, in turn, triggers a delay unit 518 to allow for settling of the multiplexer 156 before passing reticle signals therethrough. The trailing edge of the delay unit output 902 resets a flip-flop 520 and is fed through OR gate 523 to trigger a delay unit 524. The delayed pulse 907 from the delay unit 524 triggers a one-shot 532 having an output connected to the Z-axis control of the cathode ray tube 66 through the multiplexer. Subsequent triggering of the one-shot 532 by pulses from the delay unit 524 are obtained from the clock 522 which is enabled when the flip-flop 520 was reset.

X-Y positioning of the reticle marks at the face of the screen is under control of output signals 908 and 910 (FIG. 11) from D/A converters 528 and 530 connected to the cathode ray tube deflection circuits through reticle channels of the multiplexer 156. Inputs for the D/A converters are obtained from the PROM 526 which is addressed by the counter 516 output. With the illustrated arrangement the counter 516 is preset to begin counting at any one of three starting positions depending upon the reticle to be displayed, i.e. 1X, 2X, or 1X with 2X field indicator. Signals for presetting the counter are obtained from the decoder 512, and the counter is preset upon receipt of a load signal 900 from the one-shot 214 at the start of the reticle cycle. One of three different inputs is supplied to the decoder to provide one of three outputs therefrom, dependent upon the settings of the 1X-2X and 2X field indicator switches 90-1 and 94. D/A 528 and 530 outputs 908 and 910 for 1X and 2X operation are shown in FIG. 11. At the end of the reticle display the PROM 526 outputs the same X-Y signals which are decoded by decoder 533, the output 912 from which sets the flip-flop 520 to stop the clock 522, and disables the one-shot 532 to prevent the last clock pulse from triggering the one-shot.

The invention having been described in detail in accordance with the requirements of the Patent Statutes, various changes and modification will suggest themselves to those skilled in this art. With the present arrangement, 'real-time' ultrasonic B-scan image and Doppler profile displays are provided whereby a motion display of interfaces and scatterers is provided. It will be apparent, however, that the system output may be supplied to video signal storage means, such as video tape, or may be connected through a scan converter, or the like, before display of the signals. The use of the term real-time herein is not intended to preclude such arrangements. Also, with the present arrangement periodic updating of the sample and hold circuit 382 and 384 during the time normally employed to acquire and display one line of B-scan display is shown. Obviously, such updating may be performed between selected B-scan lines, if desired. It is intended that the above and other such changes and modifications shall fall within the spirit and scope of the invention as defined in the appended claims.

We claim:

1. In a real time ultrasonic imaging system having first and second operating modes for selectively providing signals representative of a B-scan image of physical characteristics of a section of the interior of a body while functioning in a first operating mode and signals representative of an enlarged B-scan image of a portion of said section while functioning in a second operating mode, said system comprising, pulse-echo means including transducer means for recurrently beaming pulses of ultrasonic waves into the body and for receiving reflections for discontinuities within the body, means for producing recurrent scanning movement of the ultrasonic pulse beam, first and second selectively operable timing means for controlling operation of said pulse-echo means for recurrent operation during the entire scanning movement of the pulse beam while in said first operating mode, and for recurrent operation during only a portion of the scanning movement while in said second operating mode.

2. In a real time ultrasonic imaging system as defined in claim 1 wherein, said means for producing recurrent scanning movement of the ultrasonic pulse beam comprises means for supporting the transducer means for recurrent movement along a path adjacent the body, which path is the same for both said first and second operating modes, said first and second timing means including means for producing master timing pulses at a rate dependent upon the rate of movement of the transducer means, said first timing means including means responsive to master timing pulses produced along the entire path of travel of said transducer means, and said second timing means including means responsive to master timing pulses produced along only a portion of the path of travel of said transducer.

3. In a real time ultrasonic imaging system as defined in claim 2 wherein said first timing means includes pulse divider means for dividing said master timing pulses.

4. In a real time ultrasonic imaging system as defined in claim 3 wherein the number of timing pulses from said pulse divider during operation in said first operating mode substantially equals the number of timing pulses from said second timing means produced during operation in said second operating mode.

5. In a real ultrasonic imaging system as defined in claim 3 wherein the transducer means is movable back and forth along a straight line path for linear scanning movement thereof, said system including,
   visual indicating means comprising a screen and means for producing an indicating spot on the screen having an intensity related to received reflected ultrasonic waves,
   one first and second deflection means selectively connected to the visual indicating means for effecting scanning movement of said spot in one direction in synchronism with said first and second selectively operable timing means, respectively, and
   another first and second deflection means selectively connected to the visual indicating means for effecting movement of said spot in a transverse direction in synchronism with the movement of said transducer means along its entire path of travel and along only said central portion of said path, respectively.

6. In a real time ultrasonic imaging system as defined in claim 5 including,
   field indicating means operable during the first operating mode for indicating on said screen the section of the interior of the body to be imaged when switching to the second operating mode.

7. In a real time ultrasonic imaging system as defined in claim 5 including,
   reticle generating means for the generation of tick mark signals for display at said screen, and
   means for simultaneously generating and displaying said tick mark signals between selected operations of said B-scan pulse-echo means.

8. In a real time ultrasonic imaging system as defined in claim 7 wherein said means for simultaneously generating and displaying said tick mark signals between selected operations of said B-scan pulse-echo means includes multiplexer means for multiplex B-scan and tick mark signal display at said screen.

9. In a real time ultrasonic imaging system as defined in claim 1 including,
   visual indicating means including a screen and means for producing an indicating spot on the screen,
   pulse Doppler transmitting and receiving means asynchronously operated relative to operation of said pulse-echo means,
   means for intensity modulating said indicating spot in accordance with the strength of the received reflections during operation of said pulse-echo means and in accordance with received Doppler signals from said pulse Doppler receiving means between selected operations of said pulse-echo means.

10. In an ultrasonic method of real time B-scan imaging of physical characteristics of the interior of a body for selectively imaging a section of the body in one operating mode and a portion thereof in another operating mode comprising,
    recurrently sweeping transducer means along a predetermined path at a predetermined rate,
    generating master timing signals at a rate in synchronism with the sweeping motion of the transducer means,
    in one operating mode, pulse dividing said master timing signals and using the divided master timing pulses for timing pulsed B-scan operation including production of an ultrasonic image at a display means, and
    in another operating mode, selecting master timing pulses which occur only during the central portion of the B-scan transducer sweep for timing B-scan operation for production of an enlarged image display of the central portion of the section imaged in the one operating mode.

11. In an ultrasonic method of real time B-scan imaging as defined in claim 10 wherein the displays for both the one and another operating modes are of substantially equal size comprising video frames which include substantially equal numbers of scan lines.

12. In an ultrasonic method of real time B-scan imaging of physical characteristics of the interior of a body for selectively imaging a section of the body in one operating mode and a portion thereof in another operating mode comprising,
    recurrently sweeping transducer means back and forth along a given path at substantially a sinusoidally varying rate,
    generating master timing pulses at a sinusoidally varying rate in synchronism with the sweep rate of the transducer means,
    in one operating mode, pulse dividing said master timing pulses and using the divided master timing pulses for timing pulsed B-scan operation including production of an ultrasonic image at a display means, and
    in another operating mode, selecting master timing pulses which occur only during the central portion of the B-scan transducer sweep for timing B-scan operation for production of an enlarged image display of the central portion of the selected image in the one operating mode.

13. In apparatus for simultaneously imaging ultrasonic reflections from a section within an object and displaying a Doppler profile along a line substantially in said imaged section,
    a pulsed real-time B-scan imaging system for periodically providing video signal fields comprising recurrent video signal lines,
    a simultaneously, asynchronously, operated pulsed Doppler system for obtaining Doppler profile signals comprising a plurality of analog signal levels, and
    visual display means for the simultaneous superimposed visual display of said real-time pulsed B-scan video signals and Doppler profile signals.

14. In apparatus as defined in claim 13 wherein Doppler profile signals are displayed between selected B-scan video signal lines.

15. In apparatus as defined in claim 13 including,
    multiplexer means for connection of said video signal from said B-scan system and Doppler profile signals to said visual display means.

16. In apparatus as defined in claim 3 including,
    Doppler cursor signal generating means having an output connected to said visual display means, and
    means for operating said Doppler cursor signal generating means between selected B-scan video signal lines for simultaneous visual display of said Doppler cursor, Doppler profile, and B-scan signals.

17. In apparatus as defined in claim 13 including, reticle signal generating means having an output connected to said visual display means, and
means for operating said reticle signal generating means between selected B-scan video signal lines for simultaneous superimposed visual display of said reticle, B-scan and Doppler profile signals.

18. In apparatus as defined in claim 13 wherein,
said B-scan and Doppler systems include B-scan and Doppler transducers, respectively, independently movable along parallel linear paths,
said B-scan system including means for periodically sweeping said B-scan transducer back and forth along its path of travel,
said Doppler system including manually controlled means for positioning said Doppler transducer along its path of travel.

19. In apparatus for simultaneously imaging ultrasonic reflections from a section within an object and displaying a Doppler profile along a line substantially in said imaged section,
a pulsed real-time B-scan system for periodically providing video signal fields comprising recurrent video signal lines,
a pulsed Doppler system for obtaining Doppler profile signals comprising a plurality of analog signal levels,
said B-scan and Doppler systems including B-scan and Doppler transducers, respectively, movable along parallel linear paths,
said B-scan system including means for periodically sweeping said B-scan transducer back and forth along its path of travel,
said Doppler system including manually controlled means for positioning said Doppler transducer along its path of travel, said manually controlled means including a control stick which is movable in one direction to control the transducer position, is movable in another direction to control the depth at which said Doppler profile signal begins, and is rotatable to control the Doppler profile length, and
visual display means for the simultaneous superimposed visual display of said real-time pulsed B-scan video signals and Doppler profile signals.

20. Ultrasonic imaging and Doppler profile display means comprising,
pulsed B-scan ultrasonic imaging means including means for recurrently acquiring pulsed B-scan video line signals of a section within a body and visual display means for raster scan displaying the same,
pulsed Doppler ultrasonic means for acquiring a plurality of analog signals related to the Doppler frequency of signals from different depths along a line within the body, and
means for recurrently sequentially displaying said analog signals at said display means between selected video raster scanning lines of B-scan display for simultaneous real-time representation of said Doppler-related signals and said B-scan signals.

21. In the ultrasonic imaging and Doppler display means as defined in claim 20 wherein said visual display means comprises a cathode ray tube.

22. In the ultrasonic imaging and Doppler display means as defined in claim 20 wherein the Doppler frequency signals are obtained from along a line which intersects the B-scan imaged plane.

23. In a combination ultrasonic pulsed B-scan and pulsed Doppler system for the simultaneous display of a real-time B-scan image of physical characteristics of a section of the interior of a body and of a superimposed Doppler profile along a line substantially in said imaged section,
focused B-scan and Doppler ultrasonic transducer means having independently relatively movable intersectable beam axes,
means for recurrently energizing said B-scan transducer means at a center frequency for recurrent broad-band pulse insonification of the body along the section to be imaged,
means including said B-scan transducer means for converting B-scan echo signals received from discontinuities within the body to equivalent electrical signals,
B-scan receiver means responsive to electrical signals from said B-scan transducer means for providing recurrent lines of video signal,
visual display means,
means for connecting the video signal output from said B-scan receiver means to said visual display means as said lines of video signal are produced to provide a real-time B-scan image at the visual display means,
means for recurrently energizing said Doppler transducer means at a frequency removed from the B-scan center frequency at an asynchronous rate with respect to the B-scan operation,
means including said Doppler transducer means and demodulating means for converting Doppler echo signals received from discontinuities within the body to equivalent Doppler electrical signals,
a plurality of sample and hold means sequentially operated to sequentially sample the Doppler electrical signals,
a plurality of frequency to voltage converter means responsive to outputs from individual sample and hold means, and
means operable between selected B-scan lines of video signal display for sequentially reading out signals from said frequency to voltage converter means to said visual display means for the simultaneous display of said real time B-scan image and a real time display of Doppler profile signals.

24. In a combination ultrasonic pulsed B-scan and pulsed Doppler system as defined in claim 23 wherein,
said means for reading out said signals from said frequency voltage converter means comprises a commutator which is clocked between selected B-scan lines of video signal display.

25. In a combination ultrasonic pulsed B-scan and pulsed Doppler system as defined in claim 23 wherein,
said frequency to voltage converter means include low pass filters in the outputs thereof, and wherein said means for reading out said Doppler signals to said visual display means comprise a commutator for sequentially connecting the low pass filtered outputs from said frequency to voltage converter means to said visual display means.

26. In a combination ultrasonic pulsed B-scan and pulsed Doppler system for the simultaneous display of a real-time B-scan image of physical characteristics of a section of the interior of a body and of a superimposed Doppler profile along a line substantially in said imaged section,
focused B-scan and Doppler ultrasonic transducer means having intersectable beam axes, means for recurrently energizing said B-scan transducer means at a center frequency for recurrent broad-band pulse insonification of the body along the section to be imaged,
means including said B-scan transducer means for converting B-scan echo signals received from discontinuities within the body to equivalent electrical signals,
B-scan receiver means responsive to electrical signals from said B-scan transducer means for providing recurrent lines of video signal,
visual display means,
means for connecting the video signal output from said B-scan receiver means to said visual display means as said lines of video signal are produced to provide a real-time B-scan image at the visual display means,
means for recurrently energizing said Doppler transducer means at a frequency removed from the B-scan center frequency at an asynchronous rate with respect to the B-scan operation,
means including said Doppler transducer means and demodulating means for converting Doppler echo signals received from discontinuities within the body to equivalent Doppler electrical signals,
a plurality of sample and hold means sequentially operated to sequentially sample the Doppler electrical signals,
a plurality of frequency to voltage converter means responsive to outputs from individual sample and hold means, and
means comprising a commutator which is clocked between selected B-scan lines of video signal display for sequentially reading out signals from said frequency to voltage converter means to said visual display means for the simultaneous display of said real time B-scan image and a real time display of Doppler profile signals,
said means for connecting the video signal output from said B-scan receiver to said video display means and said means for reading out said signals from said frequency to voltage converter means including multiplexer means.

27. In a combination ultrasonic pulsed B-scan and pulsed Doppler system for the simultaneous display of a real-time B-scan image of physical characteristics of a section of the interior of a body and of a superimposed Doppler profile along a line substantially in said image section,
focused B-scan and Doppler ultrasonic transducer means having intersectable beam axes,
means for recurrently energizing said B-scan transducer means at a center frequency for recurrent broad-band pulse insonification of the body along the section to be imaged,
means including said B-scan transducer means for converting B-scan echo signals received from discontinuities within the body to equivalent electrical signals,
B-scan receiver means responsive to electrical signals from said B-scan transducer means for providing recurrent lines of video signal,
visual display means comprising a screen and means for producing an indicating spot on the screen,
means for connecting the video signal output from said B-scan receiver means to said visual display means as said lines of video signal are produced to provide a real-time B-scan image at the visual display means,
first B-scan deflection means for effecting scanning movement of the spot in synchronism with said recurrent lines of video signal provided by said B-scan receiver,
means for supporting said B-scan transducer means for recurrent scanning movement across the section of the interior of the body to be imaged,
second B-scan deflection means for effecting movement of said spot in a transverse direction in synchronism with the position of the B-scan transducer means,
means for recurrently energizing said Doppler transducer means at a frequency removed from the B-scan center frequency at an asynchronous rate with respect to the B-scan operation,
means including said Doppler transducer means and demodulating means for converting Doppler echo signals received from discontinuities within the body to equivalent Doppler electrical signals,
a plurality of sample and hold means sequentially operated to sequentially sample the Doppler electrical signals,
a plurality of frequency to voltage converter means responsive to outputs from individual sample and hold means,
means operable between selected B-scan lines of video signal display for sequentially reading out signals from said frequency to voltage converter means to said visual display means for the simultaneous display of said real time B-scan image and a real time display of Doppler profile signals, and
first Doppler deflection means operable between first and second voltage levels over a selected portion of the first B-scan deflection means for effecting scanning movement of the spot in synchronism with operation of the means for reading out signals from said frequency to voltage converter means,
said signals read out from said frequency to voltage converter means being supplied as second Doppler deflection signals for deflection of the spot in a transverse direction in an amount related thereto from a reference signal level determined by the position of the Doppler transducer means across the imaged section.

28. In a combination ultrasonic pulsed B-scan and Doppler system as defined in claim 27 including,
means for periodically simultaneously operating at least portions of said pulsed B-scan and pulsed Doppler systems for periodically establishing said first and second voltage levels between which said first Doppler deflection means operates for proper registration of the B-scan and Doppler displays.

29. In a combination ultrasonic real time B-scan imaging and pulsed Doppler method comprising,
generating recurrent ultrasonic wave pulses to insonify a section of an object under observation for B-scan imaging,
receiving reflected wave pulses and converting the same to corresponding electrical signals,
displaying a real time B-scan image of the insonified section of the object,
asynchronously generating recurrent wave pulses for the pulsed Doppler method along a beam which intersects the B-scan imaged section, while recurrently generating said ultrasonic wave pulses for B-scan imaging, receiving reflected Doppler wave pulses from along the Doppler beam axis and converting the same to a plurality of analog voltages related to the Doppler frequency of waves reflected from different points along the Doppler beam axis, and sequentially reading out the analog voltages between selected B-scan operations for the simultaneous superimposed display of the analog voltages with the pulsed B-scan image.

30. In a combination ultrasonic real time B-scan imaging and pulsed Doppler method as defined in claim 29 wherein the analog voltages are sequentially read out through use of a commutator.

31. Manually operated mechanism for one-hand control of a plurality of variable electrical means comprising, a pivotal control stick which includes an outer end which is rotatable about the control stick axis, first, second and third manually variable potentiometers included in an ultrasonic pulsed Doppler profile system comprising pulsed Doppler transmitter/receiver means connected to a movable ultrasonic transducer, and visual display means for the visual display of Doppler profile signals, means connecting said first potentiometer to said control stick for control thereof upon pivotal movement of said control stick in a first direction, means connecting said second potentiometer to said control stick for control thereof upon pivotal movement of said control stick in a second direction orthogonal to said first direction, and means connecting said third variable electrical means to said control stick for control thereof upon rotation of the outer end of the control stick about the control stick axis, said ultrasonic pulsed Doppler profile system including, means under control of said first potentiometer for controling the position of said ultrasonic transducer, means under control of said second potentiometer for controling the delay between operation of said pulsed Doppler transmitter and Doppler receiver means, and means under control of said third potentiometer for controling the length of time operation of said Doppler receiver means.

32. In ultrasonic apparatus for displaying a Doppler profile along a line from within an object comprising, a pulsed Doppler system including transducer means for obtaining Doppler profile signals comprising a plurality of analog signal levels, means for visual display of said Doppler profile signals, manually controlled means for positioning said transducer means along a linear path, said manually controlled means comprising, a control stick which is movable in one direction for controlling the transducer position, is movable in another direction for controlling the depth at which said Doppler profile signal begins, and is rotatable for controlling the Doppler profile length.

33. In ultrasonic apparatus for displaying a Doppler profile as defined in claim 32 including, a pulsed real-time B-scan system for imaging ultrasonic reflections from a section within the object intersected by the line along which said Doppler profile signals are obtained, and means for the simultaneous superimposed visual display of said real-time pulsed B-scan image and Doppler profile signals at said visual display means.

* * * * *